United States Patent [19]

Brown et al.

[11] Patent Number: 5,866,611

[45] Date of Patent: Feb. 2, 1999

[54] THERAPEUTIC AMINES

[75] Inventors: George Robert Brown, Wilmslow; Murdoch Allan Eakin, Macclesfield; Peter John Harrison, deceased, late of Macclesfield, by Alison Harrison, heir; Keith Blakeney Mallion, Knutsford, all of England

[73] Assignee: Zeneca Limited, London, United Kingdom

[21] Appl. No.: 157,204

[22] PCT Filed: Apr. 8, 1993

[86] PCT No.: PCT/GB93/00742

§ 371 Date: May 19, 1994

§ 102(e) Date: May 19, 1994

[87] PCT Pub. No.: WO93/20807

PCT Pub. Date: Oct. 28, 1993

[30] Foreign Application Priority Data

Apr. 9, 1993 [GB] United Kingdom ............... 9207855

[51] Int. Cl.⁶ .................. A61K 31/165; A61K 31/19; A61K 31/17; A61K 31/275

[52] U.S. Cl. .................. 514/630; 514/522; 514/538; 514/563; 514/597; 514/603; 514/618; 514/620; 514/629; 514/654; 514/824; 558/414; 560/45; 564/49; 564/51; 564/86; 564/124; 564/126; 564/127; 564/162; 564/164; 564/165; 564/221; 564/223; 564/353; 564/354

[58] Field of Search .................. 564/124, 126, 564/127, 221, 223, 353, 354, 86; 514/629, 654, 824, 538, 522, 603; 560/45; 558/414

[56] References Cited

U.S. PATENT DOCUMENTS

| | | | |
|---|---|---|---|
| 2,824,872 | 2/1958 | de Lassauniere | 564/353 |
| 3,076,845 | 2/1963 | Clinton et al. | 260/562 |
| 3,342,678 | 9/1967 | Berger et al. | 167/65 |
| 3,674,807 | 7/1972 | Buzzolini | 260/326.5 |
| 4,074,998 | 2/1978 | Lacefield | |
| 4,471,116 | 9/1984 | Davidson et al. | 544/43 |

FOREIGN PATENT DOCUMENTS

| | | |
|---|---|---|
| 394440 | 5/1989 | European Pat. Off. . |
| 424525 | 6/1989 | European Pat. Off. . |
| 0394440 | 10/1990 | European Pat. Off. . |
| 1079622 | 4/1960 | Germany ............... 564/223 |
| 2654646 | 6/1977 | Germany . |
| 54-30184 | 3/1979 | Japan . |

OTHER PUBLICATIONS

Takahashi et al. "Synthesis of Basic Phenol Alkyl Ethers" *Chem. Abst* 20010f. (1958).

Cervena, Irena, Preparation of 2–(methylaminoalkoxy)biphenyls as antidepressants and intermediates, CA115(5), 28 Feb. 1991, p. 785, 49081j.

Cervena, I., et al, Potential Antidepressants: 2–(Aminoalkoxy)Biphenyls and Some Related ω–Substituted 2–Alkoxybiphenyls, Collec. Czech. Chem. Commun., 1989, pp.,1966–1978.

Lever, et al., Inhibitors of Dihydropteroate Synthase: . . . 5–Nitrosoisocytosine–p–Aminobenzoic Acid Analogues, J. Med. Chem., 1986, pp. 665–670.

Mitani et al., Novel Phenoxyalkylamine . . . Activities of α–Alkyl–α–[(phenoxypropylamino)propyl]–benzeneacetonitrile Derivatives, Chem. Pharm. Bull., 1988, pp. 373–385.

Patel et al, Potental Local Anaestics Part–VIII, J. Indian Chem. Soc., May, 1973, pp. 337–340.

Pedrazzoli et al. Chem Abst. 65:12128h, 1966.

*Primary Examiner*—Peter O'Sullivan
*Attorney, Agent, or Firm*—Pillsbury Madison & Sutro, LLP Intellectual Property Group

[57] ABSTRACT

Compounds of formula I, and their pharmaceutically acceptable salts,

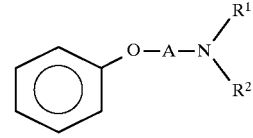

in which $R^1$ and $R^2$ are hydrogen, alkyl, cycloalkyl, cycloalkylalkyl, phenylalkyl or alkenyl; or $NR^1R^2$ is a heterocyclic group; A is trimethylene optionally substituted by alkyl and the phenyl ring is optionally substituted by substituents such as halogeno, alkenyl, amino, cyano, ureido, alkyl, carbamoylalkyl, alkanoylamino, alkoxycarbonyl, N-alkyl-alkanoylamino, alkanoyl and amines thereof; are inhibitors of squalene synthese and hence useful in treating diseases in which a lowering of cholesterol is desirable. As well as the use of these compounds in medicine, novel compounds, processes for their preparation and pharmaceutical compositions are also referred to.

13 Claims, No Drawings

THERAPEUTIC AMINES

This is a 371 of PCT/GB93/00742 filed 8 Apr. 1993.

FIELD OF THE INVENTION

This invention relates to phenoxypropylamine derivatives which possess the pharmacologically useful property of inhibiting squalene synthase and are hence useful in treating diseases or medical conditions such as hypercholesterolemia and atherosclerosis, as well as other diseases and conditions in which inhibition of squalene synthase is desirable. The present invention relates to the use of such derivatives in medicine, pharmaceutical compositions containing phenoxypropylamine derivatives, novel phenoxypropylamine derivatives and processes for the preparation of novel phenoxypropylamine derivatives.

Several different classes of compounds have been reported to possess the capability of being able to lower cholesterol levels in blood plasma. For example agents which inhibit the enzyme HMG CoA reductase, which is essential for the production of cholesterol, have been reported to reduce levels of serum cholesterol. Illustrative of this class of compounds is the HMG CoA reductase inhibitor known as lovastatin which is disclosed in U.S. Pat. No. 4,231,938. Other agents which are reported to lower serum cholesterol include those which act by complexing with bile acids in the intestinal system and which are hence termed "bile acid sequestrants". It is believed that many of such agents act by sequestering bile acids within the intestinal tract. This results in a lowering of the levels of bile acid circulating in the eroheptatic system and promoting replacement of bile acids by synthesis in the liver from cholesterol, which results in an upregulation of the heptatic LDL receptor, and thus in a lowering of circulating blood cholesterol levels.

Squalene synthase (also referred to in the art as squalene synthetase) is a microsomal enzyme which catalyses the first committed step of cholesterol biosynthesis. Two molecules of farnesyl pyrophosphate (FPP) are condensed in the presence of the reduced form of nicotinamide adenine dinucleotide phosphate (NADPH) to form squalene. The inhibition of this committed step to cholesterol should leave unhindered biosynthetic pathways to ubiquinone, dolichol and isopentenyl t-RNA. Elevated cholesterol levels are known to be one of the main risk factors for ischaemic cardiovascular disease. Thus, an agent whieh inhibits squalene synthase should be useful in treating diseases and medical conditions in which a reduction in the level of cholesterol is desirable, for example hypercholesterolemia and atherosclerosis.

Thus far, the design of squalene synthase inhibitors has concentrated on the preparation of analogues of the substrate farnesyl pyrophosphate (FPP), and hence on compounds which contain phosphorus groups. For example, the preparation of phosphorous-containing squalene synthase inhibitors is reported in published European Patent Application No. 409,181; and the preparation of isoprenoid (phosphinylmethyl)phosphonates as inhibitors of squalene synthase is reported by Biller et al, J. Med. Chem., 1988, 31, 1869.

DISCLOSURE OF INVENTION

The present invention is based on the discovery that certain phenoxypropylamine derivatives are capable of inhibiting the enzyme squalene synthase, and are hence useful in treating diseases and medical conditions in which inhibition of squalene synthase is desirable.

According to the present invention there is provided the use of a compound of formula I (formula set out hereinafter together with the other chemical formulae referred to herein), or a pharmaceutically acceptable salt thereof, wherein:

$R^1$ and $R^2$ are independently selected from hydrogen, (1–10C)alkyl, (3–10C)cycloalkyl, (3–6C)cycloalkyl(1–4C)alkyl, phenyl(1–4C)alkyl and (2–10C)alkenyl; or $R^1$ and $R^2$ together define the group —DZB—, thereby completing a ring which includes the adjacent nitrogen atom, in which D and B are independently selected from ethylene and trimethylene, Z is a direct bond between D and B, or an oxy, thio, methylene, ethylidene or isopropylidene link or a group of formula =NR3 in which R3 is hydrogen, (1–6C)alkyl, phenyl or benzyl;

A is trimethylene which is optionally substituted by one or more (1–4C)alkyl groups; and the phenyl ring is optionally unsubstituted or substituted by one or more substituents independently selected from halogeno, hydroxy, hydroxy(1–6C)alkyl, amino, (1–6C)alkylamino, di-[(1–6C)alkyl]amino, nitro, cyano, carboxy, carbamoyl, N-(1–6C)alkylcarbamoyl, di-N,N-[(1–6C)alkyl]carbamoyl, carbamoyl(1–4C)alkyl, N-(1–6C)alkylcarbamoyl(1–4C)alkyl, di-N,N-[(1–6C)alkyl]carbamoyl(1–4C)alkyl, sulphamoyl, N-(1–6C)alkylsulphamoyl, di-N,N-[(1–6C)alkyl]sulphamoyl, sulphamoyl(1–4C)alkyl, N-(1–6C)alkylsulphamoyl(1–4C)alkyl, di-N,N-[(1–6C)alkyl]sulphamoyl(1–4C)alkyl, ureido, N'-(1–6C)alkylureido, N'-phenylureido, (1–10C)alkyl optionally containing one or more double bonds, phenyl, phenyl(1–4C)alkyl, (2–6C)alkynyl, (1–6C)alkoxycarbonyl, phenyl(1–4C)alkyloxycarbonyl, (1–6C)alkanoyl and oxime derivatives thereof and O-(1–6C)alkyl ethers of said oxime derivatives, (1–6C)alkanoylamino, N-[(1–6C)alkyl](1–6C)alkanoylamino, (1–6C)alkoxy, (3–7C)cycloalkyloxy, phenyloxy, (1–6C)alkoxy(1–4C)alkyl, phenyl(1–4C)alkoxy, phenyl(1–4C)alkoxy(1–4C)alkyl, (1–6C)alkylthio, (1–6C)alkylsulphinyl, (1–6C)alkylsulphonyl, halogeno(1–6C)alkyl and phenylhydroxy(1–4C)alkyl; and wherein one or more of said phenyl moieties in said optional substituents may optionally bear one or more substituents selected from halogeno, (1–6C)alkyl, (2–6C)alkenyl, (2–6C)alkynyl, (1–6C)alkoxycarbonyl, (1–6C)alkanoylamino, N-[(1–6C)alkyl](1–6C)alkanoylamino, (3–7C)cycloalkyloxy, (1–6C)alkoxy, (1–6C)alkylthio, (1–6C)alkylsulphinyl and (1–6C)alkylsulphonyl; for the manufacture of a medicament for treating diseases or medical conditions in which inhibition of squalene synthase is desirable.

The compounds of the present invention are squalene synthase inhibitors and hence possess the property of inhibiting cholesterol biosynthesis. Thus, the compounds of the present invention will be useful in treating diseases or medical conditions in which an inhibition of squalene synthase is desirable, for example those in which a lowering of the level of cholesterol in blood plasma is desirable. In particular, the compounds of the present invention will be useful in treating hypercholesteroleamia and/or ischaemic diseases associated with atheromatous vascular degeneration such as atherosclerosis. The compounds of the present invention will also be useful in treating fungal infections.

Thus, according to a further feature of the present invention there is provided a method of inhibiting squalene synthase in a warm-blooded animal (such as man) requiring such treatment, which method comprises administering to said animal an effective amount of a compound of formula I (as herein defined), or a pharmaceutically-acceptable salt thereof. In particular, the present invention provides a method of inhibiting cholesterol biosynthesis, and more particularly to a method of treating hypercholesterolemia and atheromatous vascular degeneration (such as atherosclerosis).

It will be appreciated that, depending on the nature of the substituents, certain of the compounds of formula I may possess one or more chiral centres. In such circumstances, it will be appreciated that the compounds of the invention may exist in, and be isolated in, optically active or racemic form. The invention includes any optically active or racemic form of a compound of formula I which possesses the beneficial pharmacological effect of inhibiting squalene synthase. The synthesis of optically active forms may be carried out by standard techniques of organic chemistry well known in the art, for example by, resolution of a racemic form, by synthesis from optically active starting materials or by asymmetric synthesis.

It will also be appreciated that oxime derivatives of the (1–6C)alkanoyl group will comprise aldoximes and ketoximes of formula —C(Ra)=NOH (Ra is H or alkyl), and the O-alkyl ethers of these oximes will have the formula —C(Ra)=NORb (Ra is H or alkyl, and Rb is alkyl).

It will also be appreciated certain of the compounds of formula I may exist as geometric isomers. In such circumstances, the invention includes any geometric isomer of a compound of formula I which possesses the property of inhibiting squalene synthese.

It is also to be understood that generic terms such as "alkyl" include both the straight chain and branched chain groups such as butyl and tert-butyl. However, when a specific term such as "butyl" is used, it is specific for the straight chain or "normal" butyl group, branched chain isomers such as "t-butyl" being referred to specifically when intended.

Particular values for optional substituents which may be present on a phenyl ring include, for example:
for halogeno, fluoro, chloro, bromo or iodo;
for hydroxyalkyl, hydroxymethyl, 2-hydroxyethyl, 3-hydroxypropyl, 1-hydroxypropyl and 1-hydroxyethyl;
for alkylamino, (1–4C)alkylamino such as methylamino, ethylamino, propylamino and butylamino;
for dialkylamino, di-[(1–4C)alkyl]amino, such as dimethylamino, diethylamino, methylpropylamino and methylethylpropylamino;
for alkylcarbamoyl, N-methylcarbamoyl, N-ethylcarbamoyl and N-propylcarbamoyl;
for dialkylcarbamoyl, N,N-dimethylcarbamoyl or N,N-diethylcarbamoyl;
for carbamoylalkyl, carbamoylmethyl and carbamoylethyl;
for alkylcarbamoylalkyl, N-methylcarbamoylmethyl, N-ethylcarbamoylmethyl, N-methylcarbamoylethyl;
for dialkylcarbamoylalkyl, N,N-dimethylcarbamoylmethyl and N,N-diethylcarbamoylmethyl;
for alkylsulphamoyl, N-methylsulphamoyl, N-ethylsulphamoyl and N-propylsulphamoyl;
for dialkylsulphamoyl, N,N-dimethylsulphamoyl and N,N-diethylsulphamoyl;
for sulphamoylalkyl, sulphamoylmethyl and sulphamoylethyl; for alkylsulphamoylalkyl, N-methylsulphamoylmethyl, N-ethylsulphamoylmethyl, N-methylsulphamoylethyl;
for dialkylsulphamoylalkyl, N,N-dimethylsulphamoylmethyl and N,N-diethylsulphamoylmethyl;
for alkyluriedo, N'-methylureido, N'-ethylureido, N'-prpoylureido, N'-isopropylureido or N'-butylureido;
for an alkyl when it (2–6C)alkenyl such as allyl, prop-2-enyl, contains one or more but-2-enyl, or 2-methyl-2-propenyl; or double bonds, (4–10C)alkdienyl such as 2,6-hexadienyl or geranyl;
for alkyl, (1–6C)alkyl, such as methyl, ethyl, propyl, isopropyl, butyl, isobutyl or sec-butyl;
for phenylalkyl, benzyl, 1-phenylethyl or 2-phenylethyl;
for alkynyl, prop-2-ynyl or but-2-ynyl;
for alkoxycarbonyl, methoxycarbonyl, ethoxycarbonyl or propoxycarbonyl;
for phenylalkoxycarbonyl,
for alkanoyl, formyl, acetyl, propionyl and butyryl;
for O-(1–6C)alkyl methyl, ethyl, propyl, isopropyl and butyl ethers of alkanoyl ethers; of said oximes,
for alkanoylamino, formamido, acetamido, propionamido, iso-propionamido, butyramido or iso-butyramido;
for N-alkylalkanoylamino, N-methylacetamido, N-ethylacetamido, N-methylpropionamido, N-ethylpropionamido or N-methylbutyramido;
for alkoxy, (1–4C)alkoxy, such as methoxy, ethoxy, propoxy, isopropoxy or butoxy;
for cycloalkyloxy, cyclopropyloxy, cyclobutyloxy, cyclopentyloxy, cyclohexyloxy and cycloheptyloxy;
for alkoxyalkyl, methylpropoxy, ethylethoxy, methylmethoxy, ethylethoxy and ethylpropoxy;
for phenylalkoxy, phenylmethoxy, phenylethoxy, phenylpropoxy or phenylbutoxy;
for alkylthio, methylthio, ethylthio, propylthio, isopropylthio or butylthio;
for alkylsulphinyl, methylsulphinyl, ethylsulphinyl, proplysulphinyl, isopropyl-sulphinyl or butylsulphinyl;
for alkylsulphonyl, methylsulphonyl, ethylsulphonyl, iso-propylsulphonyl or butylsulphonyl; and
for phenylhydroxyalkyl α-hydroxybenzyl.

In general, the phenyl ring is optionally unsubstituted or substituted by one, two or three substituents selected from those mentioned above. A phenyl ring present as a substituent on the phenyl ring in the compound of formula I may, in general be optionally unsubstituted or substituted by one, two or three substituents selected from those mentioned above.

Suitable values for $R^1$ or $R^2$ when alkyl include, for example, (1–4C)alkyl such as methyl, ethyl, propyl, isopropyl, butyl, isobutyl, sec-butyl and t-butyl.

Particular values for $R^1$ and $R^2$ when cycloalkyl include, for example, (3–7C)cycloalkyl, such as cyclopropyl, cyclobutyl, cyclopentyl, cyclohexyl and cycloheptyl.

Particular values for $R^1$ and $R^2$ when phenylalkyl include, for example, benzyl, 1-phenylethyl and 2-phenylethyl.

Particular values for $R^1$ and $R^2$ when cycloalkylalkyl include, for example, cyclopropylmethyl, cyclopentylmethyl and 2-(cyclohexyl)ethyl.

Particular values for $R^1$ and $R^2$ when alkenyl include, for example, allyl, prop-2-enyl, but-2-enyl and 2-methyl-2-propenyl.

Particular values for the group —DZB— include, for example, tetramethylene, ethyleneoxyethylene, ethyleneoxytriethylene, ethylenethioethylene, pentamethylene, and groups of formula —$CH_2CH_2N(R^3)$ $CH_2CH_2$— and —$CH_2CH_2N(R^3)CH_2CH_2CH_2$— in which $R^3$ is methyl, ethyl, propyl, isopropyl, butyl, phenyl or benzyl. Thus, particular values for —$NR^1N^2$ include, pyrrolidino, morpholino, piperidino and piperazino.

Particular values for an optional alkyl substituent which may be present on the trimethylene moiety of A include, for example, methyl, ethyl, propyl and butyl. In particular, A is trimethylene optionally bearing one or two such alkyl groups (especially methyl).

More particular values for A include, for example, —CH$_2$CH$_2$CH$_2$—, —CH(Me)CH$_2$CH$_2$— and —CH$_2$CH$_2$CH(Me)—.

In particular, $R^1$ and $R^2$ are independently selected from hydrogen, (1–6C)alkyl, (3–7C)cycloalkyl, phenyl(1–4C)alkyl and (2–6C)alkenyl, or $R^1$ and $R^2$ together with the adjacent nitrogen atom define a pyrrolidino, morpholino, thiomorpholino, piperidino, or piperazino group.

In particular the phenyl ring is optionally unsubstituted or substituted by one or more substituents independently selected from halogeno, hydroxy, hydroxy(1–6C)alkyl, amino, (1–6C)alkylamino, di-[(1–6C)alkyl]amino, nitro, cyano, carboxy, carbamoyl, N-(1–6C)alkylcarbamoyl, di-N,N-[(1–6C)alkyl]carbamoyl, carbamoyl(1–4C)alkyl, sulphamoyl, N-(1–6C)alkylsulphamoyl, di-N,N-[(1–6C)alkyl]sulphamoyl, sulphamoyl(1–4C)alkyl, N-(1–6C)alkylsulphamoyl(1–4C)alkyl, di-N,N-[(1–6C)alkyl]sulphamoyl(1–4C)alkyl, ureido, N'-(1–6C)alkylureido, N'-phenylureido, (1–6C)alkyl, (2–6C)alkenyl, phenyl, phenyl(1–4C)alkyl, (2–6C)alkynyl, (1–6C)alkoxycarbonyl, (1–6C)alkanoyl and oxime derivatives thereof and O-(1–6C)alkyl ethers of said oxime derivatives, (1–6C)alkanoylamino, N-[(1–6C)alkyl](1–6C)alkanoylamino, (1–6C)alkoxy, (3–7C)cycloalkyloxy, phenyloxy, (1–6C)alkoxy(1–4C)alkyl, phenyl(1–4C)alkoxy, phenyl(1–4C)alkoxy(1–4C)alkyl, (1–6C)alkylthio, (1–6C)alkylsulphinyl, (1–6C)alkylsulphonyl, halogeno(1–6C)alkyl and phenylhydroxy(1–4C)alkyl; and wherein one or more of said phenyl moieties in said optional substituents may optionally bear one or more substituents selected from halogeno, (1–6C)alkyl and (1–6C)alkoxy.

In general it is preferred, for example, that A is trimethylene [—CH$_2$CH$_2$CH$_2$—].

In general, it is preferred that $R^1$ and $R^2$ are independently selected from hydrogen (1–6C)alkyl, (3–7C)cycloalkyl, (2–6C)alkenyl or —NR$^1$R$^2$ is a pyrrolidino, thiomorpholino, morpholino, piperidino or piperazino group.

In general it is preferred that the phenyl ring is optionally unsubstituted or bears one, two or three substituents independently selected from (2–6C)alkenyl, halogeno, amino, cyano, ureido, (1–6C)alkyl carbamoyl(1–4C)alkyl, (1–6C)alkanoylamino, (1–6C)alkoxycarbonyl, N-[(1–6C)alkyl](1–6C)alkanoylamino, (1–6C)alkanoyl and oxime derivatives thereof and O-(1–6C)alkyl ethers of said oxime derivatives.

In a preferred group of compounds $R^1$ and $R^2$ are independently selected from hydrogen, (1–6C)alkyl (such as isopropyl) and (3–7C)cycloalkyl (such as cyclobutyl or cyclopentyl); A is trimethylene which optionally bears a methyl group; and the phenyl ring is optionally unsubstituted or bears one, two or three substituents independently selected from (2–6C)alkenyl (such as allyl), halogeno (such as fluoro or chloro), amino, (1–6C)alkyl (such as propyl), carbamoyl(1–4C)alkyl (such as carbamoylmethyl), (1–6C)alkanoylamino (such as acetamido or propionamido), (1–6C)alkanoyl and oxime derivatives thereof and O-(1–6C)alkyl ethers of said oxime derivatives [such as propionyl, or HeC(NOMe)].

In a further group of compounds of interest, $R^1$ is selected from hydrogen, (1–10C)alkyl, (3–10C)cycloalkyl, (3–6C)cycloalkyl(1–4C)alkyl, phenyl(1–4C)alkyl and (2–1OC)alkenyl; and $R^2$ is isopropyl or (3–6C)cycloalkyl;

A is trimethylene which is optionally substituted by one or more (1–4C)alkyl groups; and the phenyl ring is optionally unsubstituted or substituted by one or more substituents independently selected from halogeno, hydroxy, hydroxy(1–6C)alkyl, amino, (1–6C)alkylamino, di-[(1–6C)alkyl]amino, nitro, cyano, carboxy, carbamoyl, N-(1–6C)alkylcarbamoyl, di-N,N-[(1–6C)alkyl]carbamoyl, carbamoyl(1–4C)alkyl, N-(1–6C)alkylcarbamoyl(1–4C)alkyl, di-N,N-[(1–6C)alkyl]carbamoyl(1–4C)alkyl, sulphamoyl, N-(1–6C)alkylsulphamoyl, di-N,N-[(1–6C)alkyl]sulphamoyl, sulphamoyl(1–4C)alkyl, N-(1–6C)alkylsulphamoyl(1–4C)alkyl, di-N,N-[(1–6C)alkyl]sulphamoyl(1–4C)alkyl, ureido, N'-(1–6C)alkylureido, N'-phenylureido, (1–10C)alkyl optionally containing one or more double bonds, phenyl, phenyl(1–4C)alkyl, (2–6C)alkynyl, (1–6C)alkoxycarbonyl, phenyl(1–4C)alkyloxycarbonyl, (1–6C)alkanoyl and oxime derivatives thereof and O-(1–6C)alkyl ethers of said oxime derivatives, (1–6C)alkanoylamino, N-[(1–6C)alkyl](1–6C)alkanoylamino, (1–6C)alkoxy, (3–7C)cycloalkyloxy, phenyloxy, (1–6C)alkoxy(1–4C)alkyl, phenyl(1–4C)alkoxy, phenyl(1–4C)alkoxy(1–4C)alkyl, (1–6C)alkylthio, (1–6C)alkylsulphinyl, (1–6C)alkylsulphonyl, halogeno(1–6C)alkyl and phenylhydroxy(1–4C)alkyl; and wherein one or more of said phenyl moieties in said optional substituents may optionally bear one or more substituents selected from halogeno, (1–6C)alkyl, (2–6C)alkenyl, (2–6C)alkynyl, (1–6C)alkoxycarbonyl, (1–6C)alkanoylamino, N-[(1–6C)alkyl](1–6C)alkanoylamino, (3–7C)cycloalkyloxy, (1–6C)alkoxy, (1–6C)alkylthio, (1–6C)alkylsulphinyl and (1–6C)alkylsulphonyl.

In a group of compounds of particular interest, $R^1$ is hydrogen or (1–4C)alkyl; $R^2$ is isopropyl or (3–6C)cycloalkyl; A is trimethylene optionally bearing one or two (1–4C)alkyl groups; and phenyl ring is optionally unsubstituted or bears one, two or three substituents independently selected from (2–6C)alkenyl, halogeno, amino, cyano, ureido, (1–6C)alkyl, carbamoyl(1–4C)alkyl, (1–6C)alkanoylamino, (1–6C)alkoxycarbonyl, N-[(1–6C)alkyl](1–6C)alkanoylamino, (1–6C)alkanoyl and oxime derivatives thereof and O-(1–6C)alkyl ethers of said oxime derivatives.

More preferably, the phenyl ring is optionally unsubstituted or bears one, two or three substituents independently selected from (2–6C)alkenyl, halogeno, carbamoyl(1–4C)alkyl, (1–6C)alkanoylamino, (1–6C)alkanoyl and oxime derivatives thereof and O-(1–6C)alkyl ethers of said oxime derivatives.

Specific values for $R^1$ and $R^2$ include, for example, hydrogen, methyl, ethyl, isopropyl, cyclopropyl, cyclobutyl, cyclopentyl, cyclohexyl, cycloheptyl, benzyl, allyl and for —NR$^1$R$^2$, morpholino, piperazino and pyrolidino.

Specific values for optional substituents on the phenyl ring include, for example, fluoro, chloro, methyl, propyl, isopropyl, methythio, methylsulphonyl, benzyl, ethoxycarbonyl, t-butoxycarbonyl, formyl, acetyl, propionyl, butyryl, hydroxymethyl, 1-hydroxypropyl, phenyl, 4-methylphenyl, methoxypropyl, allyl, 2-methylallyl, 1-propenyl, geranyl, crotyl, acetamido, propionamido, butyramido, phenoxy, benzyloxy, cyclohexyloxy, N-methylacetamido, cyano, N,N-diethylcarbamoyl, hydroxy, benzyloxycarbonyl, amino, nitro, carboxy, N'-phenylureido, N'-isopropylureido, carbamoylmethyl, sulphamoyl, oxime derivatives of acetyl and propionyl and O-methyl and O-ethyl ethers thereof.

Specific values for the phenyl ring of particular interest include for example, the following phenyl moieties 2-allylphenyl, 2-allyl-4-fluorophenyl, 2-allyl-4-acetamidophenyl, 2-allyl-4-carbamoylmethylphenyl, 2-allyl-4-butyramidophenyl, 2-allyl-4-aminophenyl, 2-propyl-4-acetamidophenyl, 2-allyl-4-butrylphenyl and 2-allyl-4-MeC(NOMe)phenyl.

In one embodiment R1 is hydrogen and R2 is selected from (1–6C)alkyl, (3–7C)cycloalkyl, phenyl(1–4C)alkyl and (2–6C)alkenyl, or $R^1$ and $R^2$ together with the adjacent nitrogen atom define a pyrrolidino, morpholino, thiomorpholino, piperidino, or piperazino group.

In a particular embodiment the phenyl ring bears a 2- and a 4-substituent selected from those defined above, and in particular selected from (2–6C)alkenyl (such as allyl), (1–6C)alkanoylamino (such as acetamido) and halogeno (such as fluoro).

In a particular emodiment of the present invention $R^1$ is hydrogen, $R^2$ is (1–6C)alkyl;

A is trimethylene; and the phenyl ring is optionally unsubstituted or substituted by one or more substituents independently selected from halogeno, hydroxy, hydroxy(1–6C)alkyl, amino, (1–6C)alkylamino, di-[(1–6C)alkyl]amino, nitro, cyano, carboxy, carbamoyl, N-(1–6C)alkylcarbamoyl, di-N,N-[(1–6C)alkyl]carbamoyl, carbamoyl(1–4C)alkyl, N-(1–6C)alkylcarbamoyl(1–4C)alkyl, di-N,N-[(1–6C)alkyl]carbamoyl(1–4C)alkyl, sulphamoyl, N-(1–6C)alkylsulphamoyl, di-N,N-[(1–6C)alkyl]sulphamoyl, sulphamoyl(1–4C)alkyl, N-(1–6C)alkylsulphamoyl(1–4C)alkyl, di-N,N-[(1–6C)alkyl]sulphamoyl(1–4C)alkyl, ureido, N'-(1–6C)alkylureido, N'-phenylureido, (1–10C)alkyl optionally containing one or more double bonds, phenyl, phenyl(1–4C)alkyl, (2–6C)alkynyl, (1–6C)alkoxycarbonyl, phenyl(1–4C)alkyloxycarbonyl, (1–6C)alkanoyl and oxime derivatives thereof and O-(1–6C)alkyl ethers of said oxime derivatives, (1–6C)alkanoylamino, N-[(1–6C)alkyl](1–6C)alkanoylamino, (1–6C)alkoxy, (3–7C)cycloalkyloxy, phenyloxy, (1–6C)alkoxy(1–4C)alkyl, phenyl(1–4C)alkoxy, phenyl(1–4C)alkoxy(1–4C)alkyl, (1–6C)alkylthio, (1–6C)alkylsulphinyl, (1–6C)alkylsulphonyl, halogeno(1–6C)alkyl; and wherein one or more of said phenyl moieties in said optional substituents may optionally bear one or more substituents selected from halogeno, (1–6C)alkyl, (2–6C)alkenyl, (2–6C)alkynyl, (1–6C)alkoxycarbonyl, (1–6C)alkanoylamino, N-[(1–6C)alkyl](1–6C)alkanoylamino, (3–7C)cycloalkyloxy, (1–6C)alkoxy, (1–6C)alkylthio, (1–6C)alkylsulphinyl and (1–6C)alkylsulphonyl;

Particular, preferred and specific values include the appropriate values mentioned above. For example, particular values of optional substituents which may be present on a phenyl ring include those selected from halogeno, (1–10C) alkyl optionally containing one or two double bonds, (1–6C) alkoxy, (1–6C)alkanoylamino, (1–6C)alkoxycarbonyl, (1–6C)alklythio, phenyl, phenoxy, phenyl(1–4C)alkyl and phenyl(1–4C)alkoxy; and more particular values of optional substituents which may be present on a phenyl ring include, for example, allyl, acetamido, propionamido, phenyl, methylthio, chloro, benzyloxy, n-butoxy, iso-propyl, prop-1-enyl, benzyl, fluoro, ethoxycarbonyl, phenoxy, geranyl and cyclohexyloxy.

In a further emodiment of particular interest $R^1$ is hydrogen, $R^2$ is (1–4C)alkyl (especially isopropyl); A is trimethylene optionally bearing one or two methyl groups; and the phenyl ring is optionally unsubstituted or bears one, two or three substituents independently selected from (2–6C)alkenyl (especially allyl), halogeno, (1–6C) alkanoylamino (especially acetamido), (1–6C)alkanoyl and oxime derivatives thereof and O-(1–6C)alkyl ethers of said oxime derivatives.

In a further embodiment of the present invention $R^1$ and $R^2$ are independently selected from hydrogen and (1–6C) alkyl; A is trimethylene; and the phenyl ring is optionally unsubstituted or substituted by one or more substituents selected from halogeno, (1–6C)alkyl optionally containing one or more double bonds, (2–6C)alkynyl, (1–6C) alkoxycarbonyl, (1–6C)alkanoylamino, N-[(1–6C)alkyl](1–6C)alkanoylamino, (3–7C)cycloalkyloxy, (1–6C)alkoxy, (1–6C)alkylthio, (1–6C)alkylsulphinyl, (1–6C) alkylsulphonyl, phenyl, phenyloxy, phenyl(1–4C)alkyl and phenyl(1–4C)alkoxy, the phenyl ring in the latter four substituents optionally bearing one or more substituents selected from halogeno, (1–6C)alkyl, (2–6C)alkenyl, (2–6C)alkynyl, (1–6C)alkoxycarbonyl, (1–6C)alkanoylamino, N-[(1–6C)alkyl](1–6C)alkanoylamino, (3–7C)cycloalkyloxy, (1–6C)alkoxy, (1–6C)alkylthio, (1–6C)alkylsulphinyl and (1–6C)alkylsulphonyl.

In a further embodiment, $R^1$ is selected from hydrogen and (1–4C)alkyl; $R^2$ is (1–4C)alkyl (especially isopropyl); A is trimethylene; and the phenyl ring is optionally unsubstituted or substituted as described above.

In a further embodiment, $R^1$ and $R^2$ are independently selected from hydrogen and (1–6C)alkyl; A is trimethylene; and the phenyl ring is optionally unsubstituted or substituted by one, two or three substituents selected from halogeno, (1–6C)alkyl, (2–6C)alkenyl, (2–6C)alkynyl, (1–6C) alkoxycarbonyl, (1–6C)alkanoylamino, N-[(1–6C)alkyl](1–6C)alkanoylamino, (3–7C) cycloalkyloxy, (1–6C)alkoxy, (1–6C)alkylthio, (1–6C) alkylsulphinyl, (1–6C)alkylsulphonyl, phenyl, phenyloxy, phenyl(1–4C)alkyl and phenyl(1–4C) alkoxy, the phenyl moiety in the latter four substituents optionally bearing one or more substituents selected from halogeno, (1–6C)alkyl, (2–6C)alkenyl, (2–6C) alkynyl, (1–6C)alkoxycarbonyl, (1–6C)alkanoylamino, N-[(1–6C)alkyl](1–6C)alkanoylamino, (3–7C) cycloalkoxy, (1–6C)alkoxy, (1–6C)alkylthio, (1–6C) alkylsulphinyl and (1–6C)alkylsulphonyl.

In a further embodiment of interest, $R^1$ is hydrogen or (1–6C)alkyl, $R^2$ is (1–6C)alkyl; A is trimethylene; and the phenyl ring is optionally unsubstituted or substituted by one, or two, or three substituents selected from halogeno, (1–10C)alkyl optionally containing one or more double bonds, (1–6C)alkoxy, (1–6C)alkanoylamino, N-[(1–6C) alkyl](1–6C)alkanoylamino, (1–6C)alkoxycarbonyl, (1–6C) alkylthio, phenyl, phenyl(1–4C)alkyl and phenyl(1–4C) alkoxy.

In a further group of compounds, $R^1$ is hydrogen or (1–6C)alkyl, $R^2$ is (1–6C)alkyl; A is trimethylene; and the phenyl ring is substituted by one, two or three substituents selected from (2–6C)alkenyl (such as allyl), (1–6C) alkanoylamino (such as acetamido) and halogeno (such as fluoro).

In general, the compounds of formula I (or a pharmaceutically-acceptable salt thereof) will usually be administered in the form of a pharmaceutical composition, that is together with a pharmaceutically acceptable diluent or carrier, and such a composition is provided as a further feature of the present invention.

A pharmaceutical composition of the present invention may be in a variety of dosage forms. For example, it may be in the form of tablets, capsules, solutions or suspensions for oral administration, in the form of a suppository for rectal administration; in the form of a sterile solution or suspension for parenteral administration such as by intravenous or intramuscular injection.

A composition may be obtained by conventional procedures using pharmaceutically acceptable diluents and carriers well known in the art. Tablets and capsules for oral administration may conveniently be formed with a coating, such as an enteric coating (for example, one based on cellulose acetate phthalate), to minimise dissolution of the active ingredient of formula I (or a pharmaceutically-acceptable salt thereof) in the stomach or to mask unpleasant taste.

Many of the compounds of the present invention are novel compounds and these compounds and their pharmaceutically acceptable salts are provided as a further feature of the present invention.

Thus, according to the present invention there is also provided a compound of formula I, or a pharmaceutically acceptable salt thereof, wherein:

$R^1$ and $R^2$ are independently selected from hydrogen, (1–10C)alkyl, (3–10C)cycloalkyl, (3–6C)cycloalkyl(1–4C)alkyl, and (2–10C)alkenyl; or R1 and R2 together define the group —DZB—, thereby completing a ring which includes the adjacent nitrogen atom, in which D and B are independently selected from ethylene and trimethylene, Z is a direct bond between D and B, or an oxy, thio, methylene, ethylidene or isopropylidene link or a group of formula =NR3 in which R3 is hydrogen, (1–6C)alkyl, phenyl or benzyl;

A is trimethylene which is optionally substituted by one or more (1–4C)alkyl groups; and the phenyl ring is optionally unsubstituted or substituted by one or more substituents independently selected from halogeno, hydroxy, hydroxy(1–6C)alkyl, amino, (1–6C)alkylamino, di-[(1–6C)alkyl]amino, nitro, cyano, carboxy, carbamoyl, N-(1–6C)alkylcarbamoyl, di-N,N-[(1–6C)alkyl]carbamoyl, carbamoyl(1–4C)alkyl, N-(1–6C)alkylcarbamoyl(1–4C)alkyl, di-N,N-[(1–6C)alkyl]carbamoyl(1–4C)alkyl, sulphamoyl, N-(1–6C)alkylsulphamoyl, di-N,N-[(1–6C)alkyl]sulphamoyl, sulphamoyl(1–4C)alkyl, N-(1–6C)alkylsulphamoyl(1–4C)alkyl, di-N,N-[(1–6C)alkyl]sulphamoyl(1–4C)alkyl, ureido, N'-(1–6C)alkylureido, N'-phenylureido, (1–10C)alkyl optionally containing one or more double bonds, phenyl, phenyl(1–4C)alkyl, (2–6C)alkynyl, (1–6C)alkoxycarbonyl, phenyl(1–4C)alkyloxycarbonyl, (1–6C)alkanoyl and oxime derivatives thereof and O-(1–6C)alkyl ethers of said oxime derivatives, (1–6C)alkanoylamino, N-[(1–6C)alkyl](1–6C)alkanoylamino, (1–6C)alkoxy, (3–7C)cycloalkyloxy, phenyloxy, (1–6C)alkoxy(1–4C)alkyl, phenyl(1–4C)alkoxy, phenyl(1–4C)alkoxy(1–4C)alkyl, (1–6C)alkylthio, (1–6C)alkylsulphinyl, (1–6C)alkylsulphonyl, halogeno(1–6C)alkyl; and wherein one or more of said phenyl moieties in said optional substituents may optionally bear one or more substituents selected from halogeno, (1–6C)alkyl, (2–6C)alkenyl, (2–6C)alkynyl, (1–6C)alkoxycarbonyl, (1–6C)alkanoylamino, N-[(1–6C)alkyl](1–6C)alkanoylamino, (3–7C)cycloalkyloxy, (1–6C)alkoxy, (1–6C)alkylthio, (1–6C)alkylsulphinyl and (1–6C)alkylsulphonyl;

provided that when one of $R^1$ and $R^2$ is hydrogen or alkyl, the other of $R^1$ and $R^2$ is not hydrogen or alkyl.

Particular, preferred and specific values include the appropriate values mentioned above.

The present invention also provides a compound of formula I, or a pharmaceutically acceptable salt thereof, wherein:

R1 is isopropyl; R2 is selected from hydrogen, (1–10C)alkyl, (3–10C)cycloalkyl, (3–6C)cycloalkyl(1–4C)alkyl, and (2–10C)alkenyl;

A is trimethylene which is optionally substituted by one or more (1–4C)alkyl groups; and the phenyl ring is optionally unsubstituted or substituted by one or more substituents independently selected from halogeno, hydroxy, hydroxy(1–6C)alkyl, amino, (1–6C)alkylamino, di-[(1–6C)alkyl]amino, nitro, cyano, carboxy, carbamoyl, N-(1–6C)alkylcarbamoyl, di-N,N-[(1–6C)alkyl]carbamoyl, carbamoyl(1–4C)alkyl, N-(1–6C)alkylcarbamoyl(1–4C)alkyl, di-N,N-[(1–6C)alkyl]carbamoyl(1–4C)alkyl, sulphamoyl, N-(1–6C)alkylsulphamoyl, di-N,N-[(1–6C)alkyl]sulphamoyl, sulphamoyl(1–4C)alkyl, N-(1–6C)alkylsulphamoyl(1–4C)alkyl, di-N,N-[(1–6C)alkyl]sulphamoyl(1–4C)alkyl, ureido, N'-(1–6C)alkylureido, N'-phenylureido, (1–10C)alkyl optionally containing one or more double bonds, phenyl, phenyl(1–4C)alkyl, (2–6C)alkynyl, (1–6C)alkoxycarbonyl, phenyl(1–4C)alkyloxycarbonyl, (1–6C)alkanoyl and oxime derivatives thereof and O-(1–6C)alkyl ethers of said oxime derivatives, (1–6C)alkanoylamino, N-[(1–6C)alkyl](1–6C)alkanoylamino, (1–6C)alkoxy, (3–7C)cycloalkyloxy, phenyloxy, (1–6C)alkoxy(1–4C)alkyl, phenyl(1–4C)alkoxy, phenyl(1–4C)alkoxy(1–4C)alkyl, (1–6C)alkylthio, (1–6C)alkylsulphinyl, (1–6C)alkylsulphonyl, halogeno(1–6C)alkyl; and wherein one or more of said phenyl moieties in said optional substituents may optionally bear one or more substituents selected from halogeno, (1–6C)alkyl, (2–6C)alkenyl, (2–6C)alkynyl, (1–6C)alkoxycarbonyl, (1–6C)alkanoylamino, N-[(1–6C)alkyl](1–6C)alkanoylamino, (3–7C)cycloalkyloxy, (1–6C)alkoxy, (1–6C)alkylthio, (1–6C)alkylsulphinyl and (1–6C)alkylsulphonyl;

but excluding those compounds in which R1 is hydrogen $R^2$ is isopropyl, A is unsubstituted propylene, and the phenyl ring is a 2-heptylphenyl;

2-chlorophenyl; 2-acetyl-4-propionylphenyl; 3,5-dichlorophenyl;

4-(3-methoxyphenyl)phenyl; 4-benzylphenyl; 4-phenoxy; 4-benzyloxyphenyl;

4-hydroxyphenyl; or an unsubstituted phenyl moiety;

and those in which $R^1$ and $R^2$ are both isopropyl and the phenyl ring is a 2-phenoxyphenyl or a 2-(4-chlorophenoxy)phenyl moiety.

Particular, preferred and specific values include the appropriate values mentioned above.

In a preferred group of compounds (and pharmaceutically .acceptable salts), R1 is isopropyl, R2 is hydrogen or (1–4C)alkyl, A is trimethylene, and the phenyl ring is optionally substituted by one or more substituents selected from (2–6C)alkenyl, (1–6C)alkanoylamino, halogeno, carbamoyl(1–4C)alkyl, (1–6C)alkyl, a group of formula —C(Ra)=NORb wherein Ra and Rb are (1–6C)alkyl.

Particular, preferred and specific values include the appropriate values mentioned above.

Compounds of special interest include those described in the accompanying Examples and therefore these compounds, and their pharmaceutically acceptable salts are provided as a further feature of the present invention. The compounds described in Examples 9,13,17,45,66,67,28,33, 36,60,90,94 and 116 are of particular interest and are provided as a special feature of the present invention.

The compound of the present invention may be obtained by standard procedures of organic chemistry already known to be applicable to the preparation of structurally analogous compounds. Such procedures for the preparation of novel compounds of formula I, or phamaceutically acceptable salts thereof, are provided as a further feature of the present invention and are illustrated by the following preferred processes in which the various generic radicals, for example, $R^1$ and $R^2$ may take any of the meanings hereinbefore defined, and in which the phenyl ring may optionally be unsubstituted or substituted as hereinbefore defined.

Thus according to the present invention there is also provided a process for preparing a novel compound of formula I, or a pharmaceutically acceptable salt thereof, which process comprises:

(a) reacting a compound of formula II in which X is a leaving group and which the phenyl ring is optionally unsubstituted or substituted as defined above, with an amine of formula III in which $R^1$ and R2 are as defined above.

Suitable values for X include, for example, halogen (such as chloro, bromo or iodo), mesyl and tosyl.

The reaction may be carried out in an inert solvent, for example an alcohol (such as ethanol), an ether (such as tetrahydrofuran), or water, or in the absence of an additional solvent. The reaction. is generally carried out at a temperature in the range from ambient temperature to the reflux temperature of the reaction mixture.

The starting materials of formula II may be prepared, for example, by reaction of the appropriately substituted phenol with a compound of formula II$a$ in which $X^1$ and $x^2$ are suitable leaving groups as defined above. Thus in a particular example, a compound of formula II in which X is bromo may be prepared by reaction of the appropriately substituted phenol with 1,3-dibromopropane. The reaction of compounds of formula II$a$ with the appropriately substituted phenols is generally carried out in the presence of a base, for example an alkaline earth metal carbonate (such as potassium carbonate), an alkali metal hydroxide (such as sodium hydroxide) or an alkali metal hydride (such as sodium hydride). The reaction is generally carried out in a suitable solvent at a temperature from ambient temperature to the reflux temperature of the reaction mixture. Particular examples of suitable reaction conditions include the use of potassium carbonate in a solvent of butan-2-one at a temperature in the range of about 50° to 80° C.; sodium hydroxide in an alcohol (such as ethanol) or an aqueous solvent with heating at reflux; and sodium hydride in dimethylformamide.

(b) reacting a compound of formula IV in which Z is a leaving group with an appropriately substituted phenol of formula ArOH in which Ar represents a phenyl moiety which is optionally unsubstituted or substituted as defined above, in the presence of a base.

Suitable values for Z include, for example, halogen (such as chloro, bromo or iodo). Suitable bases include, for example, an alkali metal carbonate (such as potassium carbonate), alkali metal hydroxides (such as sodium hydroxide) alkali metal alkoxides (such as sodium ethoxide) and metal hydrides (such as sodium hydride). The reaction is generally carried out in a suitable solvent at a temperature from ambient temperature to the reflux temperature of the reaction mixture. Examples of suitable solvents include alcohols (such as ethanol), dimethylformamide, acetone and butan-2-one. Preferred reaction conditions include the use of sodium hydroxide in ethanol; sodium hydride in dimethylformamide; and potassium carbonate in acetone or butan-2-one.

The compounds of formula IV may be prepared by methods known in the art. For example, such compounds may be prepared by reacting a compound of formula IIa with an amine of formula III using similar conditions to those mentioned in (a) above for the reaction of a compound of formula II with an amine of formula III.

(c) for those compounds of formula I in which $R^1$ and $R^2$ are both hydrogen, reducing a compound of formula V in which the phenyl ring is optionally unsubstituted or substituted as defined above and $A^1$ is ethylene optionally bearing one or more alkyl groups.

The reaction may be carried out, for example, by catalytic hydrogenation using a catalyst such as palladium or nickel; or by means of a reducing agent such as diborane or lithium aluminium hydride. A particularly suitable method of reducing a compound of formula V comprises the use of lithium aluminium hydride in an inert solvent such as diethyl ether or tetrahydrofuran.

(d) for those compounds of formula I in which $R^1$ and $R^2$ are both hydrogen, treating a compound of formula VI (in which the phenyl ring is optionally substituted as defined above) with hydrazine.

The reaction is generally carried out in a solvent such as ethanol at a temperature from ambient temperature to the reflux temperature of the reaction mixture.

Compounds of formula VI may be prepared by reaction of the corresponding compound of formula VI$a$ in which 'hal' represents halo group such as chloro or bromo, with a source of phthalimide anions such as potassium or sodium phthalimide, in a solvent such as dimethylformamide.

It will be appreciated that in some of the reactions mentioned herein it may be necessary/desirable to protect any sensitive groups in the compounds. The instances where protection is necessary or desirable and suitable methods for protection are known to those skilled in the art. Thus, if reactants include groups such as amino, carboxy or hydroxy it may be desirable to protect the group in some of the reactions mentioned herein. Suitable protecting groups for hydroxy include, for example, silyl groups such as trimethylsilyl or t-butyldimethylsilyl, tetrahydropyranyl and esterifing groups such as a methyl or ethyl ester; and for amino groups include benzyloxycarbonyl and t-butoxycarbonyl. Carboxy groups may be protected in a reduced form such as in the form of the corresponding protected alcohol, which may be subsequently oxidised to give the carboxy group. The protecting groups may be removed at any convenient stage in the synthesis using conventional techniques well known in the chemical art.

It will also be appreciated that certain of the various optional substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of an alkyl group using an alkyl halide and Lewis acid (such as aluminium trichloride) under Friedel Crafts conditions; and the introduction of a halogeno group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl; reaction of an alkanoyl group with hydroxylamine or an alkoxyamine to give the corresponding oxime or O-alkyloxime ether; reducing an alkenyl group to an alkyl group by, for example, catalytic hydrogenation; hydrolysing an alkanoylamino group to an amino group using, for example, a base such as aqueous sodium hydroxide; hydration of an alkenyl group to a hydroxyalkyl group; reaction of a carbonyl group with a Grignard reagent to give a hydroxyalkyl group; reaction of an amino group with an anhydride to give a alkanoylamino group; reaction of an amino group with a cyanate to give a uriedo group, for example reaction of an amino group with isopropylisocyanate to give an isopropylureido group.

When a pharmaceutically-acceptable salt of a compound of the formula I is required, it may be obtained, for example, by reaction of said compound with the appropriate acid (which affords a physiologically acceptable anion), or by reaction of the compound of formula I with the appropriate base (which affords a physiologically acceptable cation) or by any other conventional salt formation procedure. In general, acid addition salts are preferred.

The reagents used as starting materials in the above processes are readily available to those skilled in the art. Many of the starting materials are commercially available, whilst the remainder may be readily prepared from commercially available materials using standard methodology well known to those skilled in the art. For example, a wide range of substituted phenols of formula 1 are commercially available and other substituted phenols may be readily prepared by standard aromatic substitution reactions or by functional group modification as mentioned above. In particular, phenols having an alkenyl substituent, such as allyl, may be readily prepared by means of a Claisen rearrangement in which the phenol is reacted with an alkenyl halide such as allyl bromide to produce the corresponding phenol ether and the phenol ether is heated to cause the phenol ether to rearrange to the corresponding phenol having an alkenyl substituent which is at the ortho or para position. Suitable reaction conditions for generating the phenol ether are reaction of the phenol with allyl bromide in the presence of a base such as potassium carbonate and a solvent such as butan-2-one and heating at reflux. Heating the phenyl ether such as at reflux in a solvent such as diphenyl ether gives rearrangement to the allyl-substituted phenols.

As mentioned previously, the compounds of formula I (and their pharmaceutically acceptable salts) are inhibitors of the enzyme squalene synthase. Thus the compounds of the present invention are capable of inhibiting cholesterol biosynthesis by inhibition of de novo squalene production.

The beneficial pharmacological properties of the compounds of the present invention may be demonstrated using one or more of the following techniques.
(a) Inhibition of Squalene synthase In this test, the ability of a compound to prevent the formation of squalene from a radioactive substrate (tritiated farnesyl pyrophosphate) is assessed.

The test compound is incubated at a concentration of 25 micromolar in 200 $\mu$l of a buffered solution containing potassium phosphate (50 mM), $MgCl_2$ (4.95 mM), KF (9.9 mM), NADPH (0.9 mM) and rat liver microsomal protein (20 $\mu$g). Rat liver microsomes are prepared by the method described in published European Patent Application No. 324,421 and stored in liquid nitrogen prior to assay. Assay vials are kept at 37° C. throughout the incubation.

The reaction is started with the addition of the substrate (1-[$^3$H]-farnesyl pyrophosphate), final concentration 20 $\mu$H, and stopped after 15 minutes reaction time with the addition of 50 $\mu$l of 4% KOH. The reaction products are separated from unreacted substrate after application to a C-18 octadecyl 1ccBond column (Analytichem Int product No. 617101). An aqueous fraction is eluted with 250 $\mu$l of 0.1M KOH. Squalene is then eluted with 1.0 ml 10% ethylacetate in hexane and radioactivity determined. The difference in radioactivity in the presence and absence of the test compound is used to determine the level of inhibition. If the test compound inhibits at greater than about 70% at 25 micromolar, it is generally re-tested at 25 and 2.5 micromolar. The $IC_{50}$ (concentration which results in a 50% inhibition of squalene production), of the test compound can be determined by testing the compound at several, for example five, concentrations predicted from the two concentration results. The $IC_{50}$ can then be determined from a plot of percentage inhibition against concentration of test compound.

In general, compounds of formula I show significant inhibition in the above test at a concentration in the range of about 0.001 to 50 $\mu$M.

By way of illustration of the squalene synthase inhibitory properties of the compound of formula I, described in Example 2 below gave an inhibition of about 74% at a concentration of 25 $\mu$M, and the compound described in Example 95 gave an inhibition of about 86% at 2.5$\mu$M.
(b) Acute rat cholesterol synthesis assay.

This is an acute in vivo test in the rat to measure de novo hepatic cholesterol synthesis from exogenously administered $^{14}$C-acetate.

Female rats (35–55 g) are housed in reverse lighting conditions (red light from 0200 h–1400 h) for a period of about 2 weeks prior to test. Animals are allowed free access to chow and drinking water throughout this period. At test, animals should weigh 125–150 g.

Test compounds may be administered by oral gavage, dissolved or suspended in 0.5% polysorbate, or by ip or iv dosing. Control animals receive vehicle alone. After 1 hour the rats are injected ip with 25 $\mu$Ci [2-$^{14}$C]-acetate (NEN DUPONT. specific activity, 45–60mCi/mmol NEC-085H, or AMERSHAN specific activity, 50–60 mCi/mmol CFA 14) in a volume of 0.25 ml saline (100 $\mu$Ci/ml). After a further hour, rats are terminally anaesthetised with halothane and a blood sample obtained from the abdominal vena cava.

1ml of plasma is lyophilised and then saponified in 2ml ethanolic KOH (1 part 33% KOH, 9 parts ethanol) at 750° C. for 2 hours. After addition of an equal quantity of water, non-saponifiable lipids are extracted with two 5ml volumes of hexane. The hexane extracts are evaporated to dryness and the residues dissolved in ethanol to determine cholesterol specific radioactivity. $ED_{50}$ values can be determined in the standard way.

In general, compounds of formula I show activity in the range of about 0.1 to 100 mg/kg.

By way of illustration, the compound described in Example 95 gave an $ED_{50}$ of 27 mg/kg.

No overt toxicity was detected when compounds of the formula I were administered at several multiples of their minimum inhibitory dose or concentration.

When used in the treatment of diseases and medical conditions in which an inhibition of cholesterol biosynthesis is desired, for example in the treatment of hypercholesterolemia or atherosclerosis, it is envisaged that a compound of formula I (or a pharmaceutically acceptable salt thereof) will be administered orally, intravenously, or by some other medically acceptable route so that a dose in the general range of, for example, 0.01 to 50 mg per kg body weight is received. However it will be understood that the precise dose administered will necessarily vary according to the nature and severity of the disease, the age and sex of the patient being treated and the route of administration.

The compounds of the present invention may, if desired, be administered together with (or sequentially to) one or more other pharmacological agents known to be useful in the treatment of cardiovascular disease, for example, together with agents such as HHG-CoA reductase inhibitors, bile acid sequestrants, other hypocholesterolaemic agents such as fibrates, for example gemfibrozil, and drugs for the treatment of coronary heart disease. As a further example, the compounds of the present invention may, if desired, be administered together with (or sequentially to) an angiotensin converting enzyme (ACE) inhibitor, such as captopril, lisinopril, zofenopril or enalapril.

The compounds of the present invention may also find utility as antifungal agents, and so the present invention also provides a method of treating fungal infections which comprises administration to an a warm blooded animal, such as man, in need of such treatment an effective amount of a compound of formula I, or a pharmaceutically acceptable salt thereof. When used in this way the compounds of the present invention may, in addition to the formulations mentioned above, be adapted for topical administration and such a composition is provided as a further feature of the present invention. Such compositions may be in a variety of forms, for example creams or lotions.

The invention will now be illustrated by the following non-limiting Examples in which, unless otherwise stated:

(i) evaporations were carried out by rotary evaporation in vacuo;

(ii) operations were carried out at room temperature, that is in the range 18°–26° C.;

(iii) yields are given for illustration only and are not necessarily the maximum attainable by diligent process development;

(iv) proton NMR spectra were normally determined at 200 MHz using tetramethylsilane (TMS) as an internal standard, and are expressed as chemical shifts (delta values) in parts per million relative to TMS using conventional abbreviations for designation of major peaks: s, singlet; m, multiplet; t, triplet; br, broad; d,doublet;

(v) all end-products were characterised by microanalysis, NMR and/or mass spectroscopy;

(vi) conventional abbreviations are used for individual radicals and recrystallisation solvents, for example, Me=methyl, Et=ethyl, Pr=Propyl, $Pr^i$=isopropyl, Bu=butyl, $Bu^i$=isobutyl, Ph=phenyl; EtOAc=ethyl acetate, $Et_2$=ether, MeCN=acetonitrile, MeOH= methanol, EtOH=ethanol, $Pr^i$:OH=2-propanol and $H_2O$=water.

EXAMPLE 1

Isopropylamine (3.2 ml) was added to a stirred suspension of 3-allyl-4-(3-bromopropyloxy)-acetanilide (1.38 g) in propan-1-ol (12 ml). The reaction mixture was heated at reflux for 17 hours. The reaction mixture was cooled and the propan-1-ol removed by evaporation to give an oil which, on trituration with ether (50 ml), gave a solid. This material was purified by recrystallisation from propan-2-ol to give 3-allyl-4-(3-isopropylaminopropoxy)acetanilide hydrobromide (1.46 g) as a colourless solid, m.p. 150°–1° C.; microanalysis, found: C, 54.8; H, 7.5; N, 7.5%; $C_{17}H_{26}N_2O_2$.HBr requires C, 55.0; H, 7.33; N, 7.54%; NMR: ($[CD_3]_2SO$): 1.23(6H, d), 1.98(3H, s), 2.06(2H, m), 3.03(2H, m), 3.35(3H, m), 4.02(2H, t), 5.05(2H, m), 5.90 (1H, m), 6.86(1H, d), 7.28(1H, d), 7.40(1H, d of d), 8.4(2H, m) and 9.70(1H, s). m/Z 291 $(M+H)^+$.

The starting bromo compound was prepared in the following manner:

1,3-dibromopropane (20.5 g) and potassium carbonate (4.80 g) were added to a stirred solution of 4-acetamido-2-allylphenol (6.4 g) in butan-2-one at ambient temperature. The stirred mixture was then heated at reflux for 18 hours. The mixture was cooled and filtered. Evaporation of the filtrate gave an oily solid which was dissolved in ether (200 ml). The ether layer was washed with sodium hydroxide solution (2M; 3×50 ml) and then with saturated brine (3×75 ml), dried, filtered and evaporated to give a solid. This material was purified by recrystallisation from ethyl acetate to give 3-allyl-4-(3-bromopropyloxy)acetanilide (5.4 g) as a colourless solid, m.p. 105°–105.5° C.; microanalysis, found: C, 54.0; H, 5.9; N, 4.5%; $C_{14}H_{18}BrNO_2$ requires C, 53.9; H, 5.8; N, 4.5%; NMR ($CDCl_3$): 2.14(3H, s), 2.32(2H, m), 3.36(2H, d), 3.60(2H, t), 4.08(2H, t), 5.04(2H, m), 5.95(1H, m), 6.81(1H, m), 7.03(1H, m), 7.16(1H, d) and 7.37(1H, d of d). m/Z 331 $(M+NH_4)$ and 312 $(M+H)^+$.

4-Acetamido-2-allyl phenol was prepared in the following manner:

Commercially available 4-acetamido phenol (1 molar equivalent), allyl bromide (1 molar equivalent) and potassium carbonate (1 molar equivalent) in butan-2-one were heated at reflux for 18 hours with stirring. The mixture was cooled, filtered and the solid residue washed with ether. The combined filtrates were evaporated and the solid residue was further purified by crystallisation from ethyl acetate-hexane to give 4-acetamido-1-allyloxy benzene as a colourless solid, m.p. 85°–86° C.

The above allyl ether was heated under reflux in diphenyl ether for 0.16 hours. The cooled reaction mixture was diluted with diethyl ether and then extracted with sodium hydroxide solution (2M). The aqueous extracts were combined and then acidified (10M HCl). The aqueous phase was extracted with ether. After evaporation of the ether, the oily residue was triturated with hexane to give a solid which was further purified by recrystallisation from ethyl acetate-hexane to give 4-acetamido-2-allyl phenol as a colourless solid, m.p. 82°–85° C.

EXAMPLES 2–43

The procedure described in Example 1 was repeated using the appropriately substituted phenol of formula 1 ($Y^3=Y^5=Y^6=H$). Thus the appropriately substituted phenol of formula 1 ($Y^3=Y^5=Y^6=H$) was reacted with 1,3-dibromopropane and the resulting product reacted with isopropylamine. There was thus obtained the following compounds of formula 3 ($Y^3=Y^5=Y^6=H$, $R^1=H$, $R^2=Pr^i$):

| EXAMPLE | $Y^2$ | $Y^4$ | SALT | M.PT (°C.) |
|---|---|---|---|---|
| 2 | Pr | BuO | HCl | 102.3 |
| 3 | H | Ph | free base | 44–45 |
| 4 | allyl | H | HBr | 106 |
| 5 | MeS | H | oxalate | 160–162 |
| 6 | H | MeCONH | HCl | 180–182 |
| 7 | H | BuO | HBr | 146–148 |
| 8 | $PhCH_2$ | H | HBr | 135–136 |
| 9 | allyl | F | HBr | 55–57 |
| 10 | EtOCO | H | HCl | 138.8 |
| 11 | H | PhO | HCl | 164–165 |
| 12 | H | $PhCH_2O$ | HCl | 211 |

-continued

| EXAMPLE | Y² | Y⁴ | SALT | M.PT (°C.) |
|---|---|---|---|---|
| 13 | geranyl | H | free base | [a] |
| 14 | H | EtOCO | HCl | 151–152 |
| 15 | H | c-hexyloxy | HCl | 161 |
| 16 | H | Br | HBr | 164–169 |
| 17 | allyl | H₂NCOCH₂ | HBr | 158.5–159 |
| 18 | PhCH₂ | EtCONH | HCl | 227–228 |
| 19 | allyl | Ph | oxalate | 179.5–181 |
| 20 | H | t-BuOCO | free base | [b] |
| 21 | H | MeSO₂ | oxalate | 175–176 |
| 22 | allyl | BuO | HCl | 116–117 |
| 23 | allyl | H₂NSO₂ | HBr | 152–153 |
| 24 | allyl | MeCON(Me) | HBr | 118–119 |
| 25 | allyl | CN | HCl | 109–110 |
| 26 | Prⁱ O | MeCONH | oxalate | 114–116 |
| 27 | Prⁱ | H | HCl | 126–127 |
| 28 | allyl | PrCONH | HBr | 139–140 |
| 29 | allyl | PhCONH | HBr | 164–165 |
| 30 | allyl | EtCONH | HBr | 133–135 |
| 31 | allyl | Buᵗ CONH | HBr | 197–200 |
| 32 | H | PrCO | HCl | 222–224 |
| 33 | Cl | MeCONH | oxalate | 169–172 |
| 34 | CHO | BuO | HCl | 90–91.5 |
| 35 | allyl | EtOCO | HCl | 103–104 |
| 36 | allyl | PrCO | HCl | 163–165 |
| 37 | allyl | MeCO | oxalate | 193–194 |
| 38 | Br | MeCONH | oxalate | 198–200 |
| 39 | H | Et₂NCO | HCl | 132.6 |
| 40 | crotyl | MeCONH | HCl | 207–210 |
| 41 | allyl | Buᵗ OCO | free base | [c] |
| 42 | allyl | EtCO | oxalate | 108–110 |
| 43 | H | MeS | HCl | 150–151.6 |

[a] oil, mass. spec. m/z 330 (M + H)
[b] gum
[c] gum

The phenols of formula 1 used as starting materials are, in general, readily available. Many of the substituted phenols of formula I are commercially available, whilst the remaining phenols may be prepared by methods well known in the art. Thus, for example the following phenols of formula I in which Y²=allyl were prepared from the corresponding phenols in which Y²=H using the method described in Example 1 for the preparation of 4-acetamido-2-allyphenol.

| Y² | Y⁴ | M.PT. (°C.) |
|---|---|---|
| allyl | H₂NCOCH₂ | 87–88 |
| allyl | Ph | [a] |
| allyl | BuO | [b] |
| allyl | H₂NSO₂ | 123–124 |
| allyl | MeCON(Me) | 118–119 |
| allyl | CN | 70 |
| allyl | PrCONH | 88–90 |
| allyl | PhCONH | 148–149 |
| allyl | EtCONH | 125.7 |
| allyl | Buᵗ CONH | 89–90.5 |
| allyl | PrCO | [c] |
| allyl | Buᵗ OCO | [d] |
| allyl | EtCO | [e] |

[a] NMR(CDCl₃): 3.47(2H,d), 4.94(1H,s), 5.15–5.26(2H,m), 5.96–6.16(1H, m), 6.65–6.69(1H,d of d) and 7.24–7.56(7H,m)
[b] Mass. spec. m/z 207 (M + H)
[c] oil
[d] oil, NMR([CD₃]₂SO): 1.5(9H,s), 2.28(2H,s), 5.0–5.1(2H,m), 5.85–6.05 (1H,m), 6.8–6.9(1H,d), 7.6–7.7(2H,m) and 10.1–10.2(1H,s).
[e] oil The phenol used as starting material in Example 9 may be prepared by the method of Merek, J., Zesz. Nauk. Univ. Jagrellon, Pr. Chem. No. 9, 1964, 77–82; the phenol used in Example 13 by the method described in CA 86: 155360s (Japanese Patent 51125030) or Yamada, S, et al, Bull. Chem. Soc. Japan (1977), 50, 750; the phenol used in Example 15 by the method of Marcinkiewicz S et al, J. Chromatography (1963), 10, 42–68; and the phenol used in Example 20 by the method described in Can. J. Pharm. Sci, (1969), 4, 96–98.

The 2-benzyl-4-propionamidophenol (used as starting material in Example 18) was prepared as follows:

Sodium nitrite (9.48 g) was added to a solution of sulphanilic acid (24.9 g) and sodium carbonate (6.78 g) whilst maintaining the temperature of the reaction mixture at 5° C. The resulting mixture was carefully poured into a mixture of concentrated hydrochloric acid (27 ml of a 28% solution) and ice (150 g). The mixture was allowed to stand for half an hour and the mixture was then added to a mixture of 2-benzylphenol (24 g), 4.7M aqueous sodium hydroxide (150 ml) and ice (150 g) whilst maintianing the temperature below 5° C. The mixture was stirred for one hour, sodium dithionite (58.8 g) was added and the mixture slowly heated to 70° C. The reaction mixture was then allowed to cool to ambient temperature to give a precipitate which was collected by filtration to give a solid (23.47 g). To a solution of this solid (20 g) in water (150 ml), propionic anhydride (32.5 g) was added and the resulting solution heated on a steam bath for two and half hours. The solution was allowed to cool to ambient temperature and to stand overnight. The mixture was then extracted with ethyl acetate (100 ml). The ethyl acetate extract was washed with 2N aqueous hydrochloric acid (2×100 ml), saturated aqueous sodium hydrogen carbonate solution (3×100 ml) and water (100 ml), dried (MgSO₄) and evaporated to give 2-benzyl-4-propionamidophenol as a dark brown tarry oil (20.72 g); NMR[CD₃OD]: 1.15(3H,t), 2.30(2H,q), 3.9(2H,s), 6.75(1H, d) and 7.05–7.3(7H,m).

The 4-methylsulphonylphenol (used as starting material in Example 21) was prepared as follows:

A suspension of potassium peroxymonosulphate (120 g) in the form of OXONE (Trademark) in water (100 ml) was slowly added to a solution of 4-methylmercaptophenol (15 g) in methanol (50 ml). The reaction mixture was stirred for 2 hours. Water (500 ml) was added and the resulting mixture extracted with ethyl acetate (200 ml and 100 ml). The ethyl acetate extracts were combined, washed with water (800 ml), dried (MgSO₄) and evaporated to give 4-methylsulphonylphenol (11.54 g) as a colourless oil which slowly crystallised on standing, NMR(CDCl₃): 3.06(3H,s), 6.80(1H,s), 6.98(2H,d) and 7.79(2H,d); m/z 190 (M+NH₄).

The 2-hydroxy-5-butoxybenzaldehyde (used as starting material in Example 34) was prepared as follows:

4-Butoxyphenol (8.3 g) was added to a stirred aqueous 10% solution of sodium hydroxide (500 ml) at a temperature of 58° C. under an atmosphere of argon. Chloroform (70 ml) was added in dropwise manner over a period of 3 hours to the reaction mixture whilst maintaining the temperature of the reaction mixture at 58° C. The reaction mixture was stirred at 58° C. for a further 1 hour, and then allowed to cool to ambient temperature and stirred at ambient temperature overnight. The reaction mixture was cooled using an ice-bath, and concentrated hydrochloric acid was added dropwise whist maintaining the temperature below 10° C. to give pH2. The solution was extracted with ethyl acetate (2×250 ml), the ethyl acetate extracts were combined, dried (MgSO₄) and evaporated to give an oil (11.3 g). This oil was purified by chromatography on silica gel (Merck 7736) using a gradient of 0–20% ethyl acetate in hexane as eluent to give 2-hydroxy-5-butoxybenzaldehyde (3.3 g), m.pt 50°–53° C.

4-Acetamido-2-isopropoxyphenol (used as starting material in Example 26) was prepared from 2-isopropoxyphenol and acetic anhydride, using the method described above for the preparation of 2-benzyl-4-propionamidophenol, as a solid, m.p. 132°–133° C.

4-Acetamido-2-chlorophenol (used as starting material in Example 33) was prepared by the method described above for the preparation of 2-benzyl-4-propionamidophenol but using 2-chlorophenol in place of 2-benzylphenol and acetic anhydride in place of propionic anhydride.

4-Acetamido-2-bromophenol (used as starting material in Example 38) was prepared by the method described above for the preparation of 2-benzyl-4-propionamidophenol, but using 2-bromophenol in place of 2-benzylphenol and acetic anhydride in place of propionic anhydride.

4-Acetamido-2-crotylphenol (used as starting material in Example 40) was prepared by the method described above for the preparation of 2-benzyl-4-propionamidophenol, but using 2-crotylphenol in place of 2-benzylphenol and acetic anhydride in place of propionic anhydride.

4-Hydroxy-N,N-diethylbenzamide (used as starting material in Example 39) was prepared in the following manner.

A solution of n-butyl lithium in hexane (1.6M, 22.87 ml) was added to a solution of diethylamine (3.74 ml) in dry tetrahydrofuran (100 ml), at ambient temperature and under an atmosphere of argon. The reaction mixture was stirred for 15 minutes. Ethyl 4-hydroxybenzoate (5 g) was then added and the reaction mixture stirred for 16 hours. Diethyl ether was added to the reaction mixture and the mixture was washed with water, dried ($MgSO_4$) and evaporated. The residue was purified by flash column chromatography on silica gel (Merck Art No. 9385) using a 1:3 (v/v) mixture of ethyl acetate/hexane as eluent to give 4-hydroxy-N,N-diethyl benzamide as a solid (1.17 g), m.p. 122.5° C.; NMR ($[CD_3]_2SO$): 1.1–1.15(6H,t), 3.2–3.4(4H,m), 6.75–6.85(2H, d), 7.15–7.25(2H,d), and 9.7(1H,s); m/z 194(M+H).

4-Acetamido-2-chlorophenol (used as starting material in Example 33) was prepared as follows.

A solution of 2-chloro-4-nitrophenol (10.4 g) in methanol (500 ml) was added to a mixture of iron (90 g, pretreated with 28% hydrochloric acid) and iron(II) sulphate (16.5 g) in water (120 ml).

The mixture was heated at reflux for 6 hours, cooled to ambient temperature and filtered. The filtrate was evaporated, and the residue treated with ether to give crude 2-chloro-4-aminophenol (10 g). The crude 2-chloro-4-aminophenol (3.5 g) was added to a mixture of water (50 ml) and acetic anhydride (5.7 ml). The reaction mixture was stirred at reflux for 2 hours. The reaction mixture was cooled to ambient temperature and the supernatant was decanted away from an oil which gave a solid on standing. The solid was purified by flash column chromatography on silica gel (Merck Art. No 9385) using a 1:2(v/v) mixture of ethyl acetate and pentane as eluent to give 2-chloro-4-acetamidophenol as an oil (1.7 g); NMR: ($[CD_3]_2SO$): 2.0(3H,s), 6.85(1H,d), 7.2(1H,m), 7.68(1H,m) and 9.8(2H, m).

4-Acetamido-2-bromophenol (used as starting material in Example 38) was prepared from 2-bromophenol using the method described above for the preparation of 4-acetamido-2-chlorophenol NMR($[CD_3]_2SO$): 2.0(3H,s), 6.88(1H,m), 7.25(1H,m), 7.7(1H,m), 9.8(1H,br s) and 9.9(1H,s).

Similarly 4-amino-2-but-2-enyl phenol (used as starting material in Example 40) was prepared from 2-but-2-enylphenol. Treatment of this phenol with acetic anhydride (using the method described above for the preparation of 4-acetamido-2,6-dichlorophenol from 4-amino-2,6-dichlorophenol) gave 4-acetamido-2-but-2-enylphenol.

EXAMPLE 44–64

The procedure described in Example 1 was repeated using the appropriately substituted phenol of formula 1 ($Y^3=Y^5=$H). Thus the appropriately substituted phenol of formula 1 ($Y^3=Y^5=$H) was reacted with 1,3-dibromopropane and the resulting product reacted with the appropriate amine of formula $R^1R^2NH$. There was thus obtained the following compounds of formula 3 ($Y^3=Y^5$=H):

| EXAMPLE | $R^1$ | $R^2$ | $Y^2$ | $Y^4$ | $Y^6$ | SALT | M.PT. (°C.) |
|---|---|---|---|---|---|---|---|
| 44 | Me | $Pr^i$ | allyl | H | H | oxalate | 113–114 |
| 45 | Me | $Pr^i$ | allyl | MeCONH | H | HBr | 121–122 |
| 46 | H | $Bu^t$ | allyl | MeCONH | H | HBr | 171–172 |
| 47 | H | $PhCH_2$ | allyl | MeCONH | H | free base | 91–92 |
| 48 | Me | $Pr^i$ | allyl | $MeSO_2$ | H | free base | [a] |
| 49 | Me | $Pr^i$ | H | EtOCO | H | HCl | 131.3 |
| 50 | Me | $Pr^i$ | H | $PhCH_2OCO$ | H | HCl | 97.1 |
| 51 | H | $Pr^i$ | Cl | PrCONH | Cl | HCl | 191–192 |
| 52 | H | $Pr^i$ | Cl | MeCONH | Cl | HCl | 204–206 |
| 53 | H | $Pr^i$ | $Pr^i$ | H | $Pr^i$ | HCl | 167–168 |
| 54 | H | $Pr^i$ | Br | MeCONH | Br | oxalate | 130 |
| 55 | H | $Pr^i$ | Cl | MeCO | Cl | oxalate | 128–131 |
| 56 | H | $Pr^i$ | allyl | MeCONH | allyl | free base | 77–77.5 |
| 57 | H | Bu | allyl | MeCONH | H | HBr | 140 |
| 58 | Me | Me | allyl | MeCONH | H | HBr | 154.3 |
| 59 | H | Pr | allyl | MeCONH | H | HBr | 143.1 |
| 60 | H | Et | Pr | MeCONH | H | HBr | 115.6 |
| 61 | Me | Et | allyl | MeCONH | H | HBr | 117.3 |
| 62 | H | $Pr^i$ | allyl | MeCO | F | oxalate | 144–146 |
| 63 | Et | Et | allyl | MeCONH | H | HCl | 199.5 |
| 64 | H | $Pr^i$ | Cl | H | Cl | HCl | 150–152 |

[a] Mass. spec. m/z 326 (M + H)

The phenols of formula I used as starting materials are readily available. Many of the substituted phenols of formula I are commercially available, whilst the remaining phenols may be prepared by methods well known in the art. Thus, for example the phenol ($Y^2$=allyl, $Y^4=MeSO_2$, $Y^3=Y^5=Y^6$=H) used as starting material in Example 48 was prepared as a solid (m.p. 70° C.) from the phenol ($Y^4=MeSO_2$, $Y^2=Y^3=Y^5=Y^6$=H) described with reference to Example 21 using the method described in Example 1 for the preparation of 4-acetamido-2-allyphenol. Similarly, the method described in Example 1 for the preparation of 4-acetamido-2-allylphenol was used to prepare the phenol of formula 1 ($Y^2=Y^6$=allyl, $Y^4$=MeCO, $Y^5=Y^6$=H) used as starting material in Example 56 as a solid (m.p. 86°–88° C.) from the phenol of formula 1 in which $Y^4$=MeCO and $Y^2=Y^3=Y^5=Y^6$=H); and to prepare the phenol of formula I ($Y^2$=allyl, $Y^4$=MeCO, $Y^3=Y^5=F=Y^6$=H) from the phenol of formula I in which $Y^4$=MeCO and $Y^2=Y^3=Y^5=F=Y^6$=H as an oil.

4-Acetamido-2,6-dichlorophenol (used as starting material in Example 52) was prepared as follows.

Acetic anhydride (7.1ml) was added to a suspension of 4-amino-2,6-dichlorophenol (5.34 g) in-water (50 ml). The mixture was stirred at reflux for 2 hours. The reaction mixture was cooled to ambient temperature and the crude product was collected by filtration, washed with water and then washed with pentane to give 4-acetamido-2,6-dichlorophenol as a solid (5.6 g), m.p. 151°–152°; NMR ($[CD_3]_2SO$): 2.0(3H,s), 7.58(2H,s) and 9.92(2H,br s); m/z 220 (M+H).

Using the method described above for the preparation of 4-acetamido-2,6-dichlorophenol (but using butyric anhydride in place of acetic anhydride) there was obtained 4-butyramido-2,-6-dichlorophenol (used as starting material in Example 51) as a solid, m.p. 146°–147°; NMR([CD$_3$]$_2$SO): 0.9(3H,t), 1.58(2H,m), 2.25(2H,t), 7.62(2H,s), 9.75 (1H,br s) and 9.85(1H,s); m/z 248(M+H).

4-Acetamido-2,6-dibromophenol (used as starting material in Example 54) was prepared from 2,6-dibromophenol and acetic anhydride, using the method described above for the preparation of 4-acetamido-2,6-dichlorophenol, as a solid, m.p. 155°–156° C.

4-Acetamido-2,6-dichlorophenol (used as starting material in Example 52) was prepared as a solid (m.p. 151°–152° C.) from 2,6-dibromophenol and acetic anhydride, using the method described above for the preparation of 4-acetamido-2,6-dichlorophenol.

3-Allyl-5-fluoro-4-hydroxyacetophenone was prepared as follows:

3-Fluoro-4-hydroxyacetophenone, prepared by the method of Helv. Chim. Acta, 72, 606, (1989), was reacted with allyl bromide using the method described in Example 1 for the preparation of 4-acetamido-2-allylphenol to give 3-allyl-5-fluoro-4-hydroxyacetophenone (used as starting material in Example 62)., NMR (CDCl$_3$): 2.55(3H,s), 3.48 (2H,m), 5.15(2H,m), 5.9(1H,d), 6.0(1H,m) and 7.6(2H,m).

EXAMPLES 65–88

The procedure described in Example 1 was repeated using the appropriately substituted phenol of formula 1. Thus the appropriately substituted phenol of formula 1 was reacted with 1,3-dibromopropane and the resulting product reacted with the appropriate amine of formula $R^1R^2NH$. There was thus obtained the following compounds of formula 3:

Thus, for example, the phenol ($Y^2$=2-methylallyl, $Y^3$=H, $Y^4$=MeCONH, $Y^5$=$Y^6$=H) may be prepared from the phenol of formula 1 in which $Y^4$=MeCONH, $Y^3$=$Y^5$=$Y^6$=H and 2-methylallylbromide using the method described in Example 1 for the preparation of 4-acetamido-2-allylphenol. Similarly, the phenols of formula 1 in which $Y^2$=allyl, $Y^3$=F, $Y^4$=MeCO, $Y^5$=$Y^6$=H; and in which $Y^2$=allyl, $Y^3$=H, $Y^4$=MeCO, $Y^5$=F and $Y^6$=H may be prepared from the phenol in which $Y^3$=F, $Y^4$=MeCO and $Y^2$=$Y^5$=$Y^6$=H using the method described in Example 1 for the preparation of 4-acetamido-2-allylphenol.

EXAMPLE 88

A solution of 3-allyl-4-(3-[N-isopropylamino]propoxy)-acetophenone (1.38 g) methoxyamine hydrochloride (0.46 g) and anhydrous sodium acetate (0.45 g) in water (5 ml) and absolute ethanol (2 ml) was heated at reflux for 18 hours. The reaction mixture was cooled to ambient temperature and extracted with ethyl acetate (2×15 ml). The ethyl acetate extracts were combined, dried (HgSO$_4$) and evaporated. The resultant oily solid was triturated with pentane, and then with diethyl ether to give 3-allyl-4-(3-[N-isopropyl-amino] propoxy)acetophenone O-methyloxime as a solid (0.20 g), m.p. 126°–128° C.; microanalysis, found: C, 63.4; H, 8.9; N, 7.9%; C$_{18}$H$_{28}$N$_2$O$_2$. 2H$_2$O requires C,63.5; H, 9.4; N, 8.3%. NMR: (CDCl$_3$): 1.50(6H,d), 2.17(3H,s), 2.48(2H,m), 3.15 (2H,t), 3.35(3H,m), 3.96(3H,s), 4.08(2H,t), 5.0(1H,m), 5.06 (1H,s), 5.90(1H,m), 6.80(1H,m) and 7.42(2H,m); m/z 305 (M+H).

The preparation of 3-allyl-4-(3-[N-isopropylamino] propoxy)-acetophenone is described in Example 37.

EXAMPLE 89

The procedure described in Example 88 was repeated using hydroxylamine hydrochloride in place of methoxyamine hydrochloride to give 3-allyl-4-(3-[N-isopropylamino]propoxy)acetophenone oxime as a solid, m.p. 194°–195° C.

| Ex. | $R^1$ | $R^2$ | $Y^2$ | $Y^3$ | $Y^4$ | $Y^5$ | $Y^6$ | Salt | M.PT(°C.) |
|---|---|---|---|---|---|---|---|---|---|
| 65 | H | c.hex | allyl | H | MeCONH | H | H | HCl | 174–6 |
| 66 | H | c.pent | allyl | H | MeCONH | H | H | HCl | 192–3 |
| 67 | H | c.but | allyl | H | MeCONH | H | H | HCl | 191–2 |
| 68 | H | cPr | allyl | H | MeCONH | H | H | HCl | 131–2 |
| 69 | H | c.hep | allyl | H | MeCONH | H | H | HCl | 157–8 |
| 70 | H | Pr$^i$ | Cl | Cl | Cl | Cl | Cl | HCl | 196–8 |
| 71 | H | Pr$^i$ | F | F | F | F | F | HCl | 175–6 |
| 72 | H | Pr$^i$ | Cl | H | H | Cl | H | HCl | 162–4 |
| 73 | H | Pr$^i$ | Pr$^i$ | H | H | Me | H | HCl | 190–1 |
| 74 | H | Pr$^i$ | 1-Me-allyl | H | MeCONH | H | H | HCl | 190–3 |
| 75 | H | Pr$^i$ | allyl | F | MeCO | H | H | OXAL | 142–3 |
| 76 | H | Pr$^i$ | allyl | H | MeCO | F | H | OXAL | 148–9 |
| 77 | H | Pr$^i$ | allyl | H | EtCO | H | H | OXAL | 108–110 |
| 78 | Pr$^i$ | Pr$^i$ | allyl | H | MeCONH | H | H | free base | 50–3 |
| 79 | H | Pr$^i$ | allyl | H | EtCO | MeO | H | OXAL | 72–77 |
| 80 | Et | Et | Ph | H | Br | H | Br | HCl | 160–162 |
| 81 | H | Pr$^i$ | H | MeS | H | H | H | HCl | 110 |
| 82 | Et | Et | H | MeS | H | H | H | OXAL | 106–108 |
| 83 | Me | Pr$^i$ | H | H | BuO | H | H | HCl | 120–121 |
| 84 | H | Pr$^i$ | Pr | H | H | H | H | HBr | 89–90 |
| 85 | H | Pr$^i$ | H | EtOCO | H | H | H | HCl | 154.7 |
| 86 | H | Pr$^i$ | H | Cl | Cl | H | H | HCl | 157–158 |
| 87 | H | t-butyl | allyl | H | MeCONH | H | H | OXAL | 200–202 |

NOTE:
OXAL = Oxalate

The phenols of formula 1 used as starting materials are readily available. Many of the substituted phenols of formula 1 are commercially available, whilst the remaining phenols may be prepared by methods well known in the art.

EXAMPLE 90

The procedure described in Example 88 was repeated using 3-allyl-4-(3-[N-isopropylamino]propoxy) butyrophenone in place of 3-allyl-4-(3-[N-isopropylamino] propoxy)acetophenone to give 3-allyl-4-(3-[N-isopropylamino]propoxy)butyrophenone O-methyloxime as a solid, m.p. 132°–134° C.

EXAMPLE 91

The procedure described in Example 88 was repeated using 3-allyl-4-(3-[N-isopropylamino]propoxy) butyrophenone in place of 3-allyl-4-(3-[N-isopropylamino] propoxy)acetophenone to give 3-allyl-4-(3-[N-isopropylamino]propoxy)butyrophenone oxime as a solid, m.p. 166°–168° C.

EXAMPLE 92

The procedure described in Example 88 was repeated using 3-allyl-4-(3-[N-isopropylamino]propoxy) butyrophenone and ethoxyamine hydrochloride to give 3-allyl-4-(3-[N-isopropylamino)propoxy)-butyrophenone O-ethyloxime as a solid, m.p. 124°–126° C.

EXAMPLE 93

The procedure described in Example 88 was repeated using 3-allyl-4-(3-[N-isopropylamino]propoxy) benzaldehyde and methoxyamine hydrochloride to give 3-allyl-4-(3-[N-isopropyl]propoxy)benzophenone O-methyloxime hydrochloride as a solid, m.p. 123.1° C. The preparation of 3-allyl-4-(3-[N-isopropylamino]propoxy) benzaldehyde is described in Example 97 below.

EXAMPLE 94

Isopropylamine (1.5 ml) was added to a stirred solution of 3-allyl-4-(3-bromopropoxy)trifluoromethylacetanilide (450mg) in propan-1-ol (8 ml). The reaction mixture was heated at reflux for 16 hours. The reaction mixture was cooled to ambient temperature and the propan-1-ol removed by evaporation to give an oil which, on trituration with ether (25 ml), gave a solid. This material was purified by recrystallisation from propan-2-ol to give 3-allyl-4-(3-[N-isopropylamino]propoxy)aniline hydrobromide (283 mg) as a solid, m.p. 169°–170° C.; microanalysis, found: C, 53.2; H, 7.8; N, 7.9%; $C_{15}H_{24}N_2O.HBr$ 0.5 $H_2O$ requires: C 53.2; H, 7.7; N 8.2% NMR: ($[CD_3]_2SO$): 1.24(6H,d), 2.03(2H,m), 3.04(2H,m), 3.23(2H,d), 3.31(1H,m), 3.92(2H,t), 4.82(1H, m), 5.07(2H,m), 5.90(1H,m), 6.40(2H,m), 6.68(1H,m) and 8.37(2H,m); m/z 249(M+H).

The starting bromo compound (m.p. 78°–79°) was prepared by the method described in Example 1 by the reaction of 4-trifluoromethylacetamido-2-allylphenol (m.p. 130-1) and 1,3-dibromopropane. The 4-trifluoromethylacetamido-2-allylphenol was prepared from 4-trifluoromethylacetamidophenol using the method described in Example 1 for the preparation of 4-acetamido-2-allyl phenol.

EXAMPLE 95

A solution of 3-allyl-4-(3-[N-isopropylamino]-propoxy) acetanilide (770 mg) in absolute ethanol (30 ml) was hydrogenated at atmospheric pressure for 3 hours over a catalyst of 10% palladium on carbon. The catalyst was removed by filtration and the filtrate was evaporated. The residue was dissolved in propan-2-ol (5 ml). Saturated ethereal hydrogen chloride was added and the precipitated solid crystallised from a mixture of propan-2-ol and diethyl ether to give 3-n-propyl-4-(3-[N-isopropylamino]propoxy)-acetanilide hydrochloride (512 mg) as a solid, m.p. 172°–50° C., microanalysis, found: C, 60.7; H, 9.2; N, 8.4%; $C_{17}H_{28}N_2O_2.HCl$ 0.5 $H_2O$ requires: C, 60.4; H, 8.90; N, 8.4%; NMR ($[CD_3]_2SO$): 0.90(3H,t), 1.25(3H,s), 1.28(3H, s), 1.53(2H,m), 2.0(3H,s), 2.12(2H,m), 2.51(2H,m), 3.03 (2H,m), 3.30(1H,m), 4.03(2H,t), 6.85(1H,d), 7.35(2H,m), 9.05(2H,m) and 9.80(1H,s); m/z 293(M+H).

EXAMPLE 96

The procedure described in Example 1 was repeated by treating 1-(3-bromopropoxy)-2-(2-prop-1-enyl)benzene with isopropylamine to give N-isopropyl-3-(2-prop-1-enylphenoxy)propylamine as a solid, m.p. 107°–109° C.

The 1-(3-bromopropyloxy)-2-(2-prop-1-enyl)benzene used as starting material was prepared as follows.

A mixture of 2-allyl-3'-bromopropoxybenzene (2.04 g) and rhodium chloride (100 mg) in ethanol (11) was heated at reflux for 2.5 hours. The mixture was cooled to ambient temperature and the ethanol removed by evaporation. Vater (300 ml) was added and the resulting suspension was extracted with ether. The ether extract was washed with saturated brine, dried ($Na_2SO_4$) and evaporated to give 2-E-propen-1-yl-3'-bromopropoxybenzene (1.20 g) as a colourless oil; NMR($CDCl_3$): 1.90(3H,d of d), 2.36(2H,m), 3.62(2H,t), 4.12(2H,m), 6.20(1H,m), 6.70(1H,d of d, J=15.86) 6.90(2H,m), 7.19(1H,m) and 7.39(1H d of d).

The 2-allyl-3'-bromopropoxybenzene was prepared from 2-allyl phenol and 1,3-dibromopropane using the standard method described in Example 1.

EXAMPLE 97

1M aqueous hydrochloric acid (2 ml) was added to 3-allyl-4-(3-[N-isopropylamino]propoxy)benzaldehyde, 2-(1,3-dioxane)acetal (200 mg) and stirred for 16 hours at ambient temperature. The reaction mixture was evaporated and the residue purified by flash column chromatography on silica gel (Merck Art No 9385) using a 90:8:2 (v/v/v) mixture of ethyl acetate/methanol/ammonia (density=0.88 g/cm$^3$) as eluent. The crude product obtained was dissolved in ethanol, acidified with saturated ethanolic hydrogen chloride solution and evaporated to give a residue which was crystallised from ethyl acetate to give 3-allyl 4-(3-[N-isopropylamino]propoxy)benzaldehyde hydrogen chloride (133 mg) as a solid, m.p. 109.1° C.; microanalysis, found; C, 62.6; H, 8.2; N, 4.6%; $C_{16}H_{23}NO_2$. HCl 0.5$H_2O$, C, 62.6; H, 8.1; N, 4.6%; NMR($[CD_3]_2SO$): 1.4–1.6(6H,d), 1.7–2.0 (2H,m), 3.2–3.5(3H,m), 3.8–4.3(2H,m), 4.9–5.1(2H,m), 5.8–6.1(1H,m), 6.9–7.0(1H,d), 7.65–7.8(2H,m), 9.4–9.8 (2H, br s) and 9.85(1H,s); m/z 262(M+H).

The 3-allyl-4-(3-[N-isopropylamino]propoxy) benzaldehyde 2-(1,3-dioxane)acetal used as a starting material was prepared as follows.

1,3-Dibromopropane (15.76 ml) and potassium carbonate (4.69 g) were added to a solution of 3-allyl-4-hydroxybenzaldehyde (5 g) in acetone and the reaction mixture heated at reflux for 16 hours. The reaction mixture was cooled to ambient temperature and filtered. The filtrate was evaporated and the residue purified by flash column chromatography on silica gel (Merck Art No 9385) using a 10:90 (v/v) mixture of ethyl acetate/hexane as eluent to give 3-allyl-4-(3-bromopropoxy)benzaldehyde (4.86 g) as an oil which slowly solidified. NMR($[CD_3]_2SO$): 2.2–2.4(2H,m), 3.35–3.50(2H,m), 3.65–3.80(2H,t), 4.2–4.3(2H,t), 5.0–5.15 (2H,m), 5.8–6.1(1H,m), 7.15–7.25(1H,d), 7.7(1H,d), 7.75–7.85(1H,q) and 9,85(1H,s).

The starting 3-allyl 4-hydroxybenzaldehyde was prepared from 4-hydroxybenzaldehyde using the method described in Example 1 for the preparation of 4-acetamido-2-allylphenol.

EXAMPLE 98

Potassium cyanate (44 mg) was added to a stirred solution of 3-benzyl-4-(3-[N-isopropylamino]propoxy)aniline dihydrochloride (222 mg) in water (5 mls). The reaction mixture was stirred for 2 hours and the resulting precipitate collected by filtration. The solid collected was purified by flash column chromatography on silica gel (Merck Art No 9385) using a 90:10:1 (v/v/v) mixture of dichloromethane/ethanol/ammonia (density=0.88 g/cm$^3$) as eluent to give a residue which was dissolved in saturated methanolic hydrogen chloride solution. The solution was evaporated to give a solid which was crystallised from ethanol to give 3-benzyl-4-(3-[N-isopropylamino]propoxy)phenylurea hydrochloride as a white solid (582 mg), m.p. 204.7° C., microanalysis, found: C, 63.6; H, 7.6; N, 10.9%; $C_{20}H_{23}N_3O$. HCl requires: C, 63.6; H, 7.47; N, 11.1%; NMR:([CD$_3$]$_2$SO): 1.2(6H,d), 2.05(2H,m), 2.9(2H,t), 3.25(1H,m), 3.85(2H,s), 4.0(2H,t), 5.7(2H,s), 6.82(1H,d), 7.05–7.3(7H,m), 8.4(1H,s), 7.5(2H, s); m/z 342(M+H).

EXAMPLE 99

2M aqueous sodium hydroxide (10 ml) was added to a solution of 3-benzyl-4-(3-[N-isopropylamino]propoxy) propanilide (1 g) in absolute ethanol (20 ml). The resulting mixture was heated at reflux for 18 hours. The mixture was cooled to ambient temperature and the ethanol removed by evaporation. Water (200 ml) was added and the resulting suspension was extracted with ethyl acetate (3×100 ml). The ethyl acetate extracts were combined, washed with saturated brine (2×100 ml), dried (MgSO$_4$) and evaporated to give an oil which crystallised on standing, to give 3-benzyl-4-(3-[N-isopropylamino]propoxy)aniline (550 mg) as a solid, m.p. 41.1° C., microanalysis, found: C, 74.8; H, 9.2; N, 9.2%; $C_{19}H_{26}N_2O$. 0.4 H$_2$O requires: C, 74.6; H, 8.8; N, 9.17%; NMR([CD$_3$]$_2$SO): 0.95(6H,d), 1.75(2H,p), 2.5–2.75 (3H,m), 3.75(2H,s), 3.85(2H,t), 4.5(2H,s), 6.3–6.4(2H,m), 6.68(1H,m) and 7.1–7.3(5H,m); m/z 299(M+H).

EXAMPLE 100

Using the procedure described above for the preparation of 4-acetamido-2,6-dichlorophenol, 3-benzyl-4-(3-[N-isopropylamino]propoxy]aniline was treated with acetic anhydride to give 3-benzyl-4-(3-[N-isopropylamino] propoxy]acetanilide as a solid, m.p. 202.5° C.

EXAMPLE 101

Sodium hydride (51 mg) was added portionwise over a period of 5 minutes to a stirred solution of N,N-dimethyl-3-[4-butoxy-2-(3-hydroxypropyl)phenoxy]propylamine (330 mg) in tetrahydrofuran (8 ml) at a temperature of 0° C. and under an atmosphere of argon. The reaction mixture was allowed to warm to 25° C. and stirred for a further 0.5 hour. The reaction mixture was cooled to 0° C. and methyl iodide (0.4 ml) added. The reaction mixture was allowed to warm to 25° C. and the reaction mixture was stirred for a further 15 hours. The reaction mixture was poured into water (15 ml) and extracted with ethyl acetate (4×15 ml). The ethyl acetate extracts were combined, washed with water (10 ml), dried (MgSO$_4$) and evaporated to give a yellow oil. The oil was purified by flash column chromatography on silica gel (Merck Art No 9385) using a 75:25:0.2 mixture of ethyl acetate, hexane, and triethylamine as eluent to give N,N-dimethyl-3-[4-butoxy-2-(3-methoxypropyl)phenoxy] propylamine as a yellow oil (70 mg), NMR ([CD$_3$]$_2$SO): 0.92(3H,t), 1.42(2H,m), 1.70(4H,m), 2.1(2H,m), 2.5(6H,s), 2.9(2H,m) and 3.2(3H,s), 3.31(2H,t), 3.9(4H,m), 6.7(2H,s), and 6.82(1H,d); m/z 324 (M+H). The N,N-dimethyl-3-[4-butoxy-2-(3-hydroxypropyl)phenoxy]propylamine used as starting material was prepared as follows.

A solution of N,N-dimethyl-3-(2-allyl-4-butoxyphenoxy) propylamine (1.8 g) in tetrahydrofuran (3 ml) was added dropwise over a period of 3 minutes to a solution of borane tetrahydrofuran complex (1M, 12.4 ml) at a temperature of 0° C. and under an atmosphere of argon. The reaction mixture was stirred at 0° C. for 3 hours. Ethanol (10 ml) was added to the reaction mixture, followed by aqueous 6N aqueous sodium hydroxide and hydrogen peroxide solution (30%, 12 ml). The mixture was then heated at 50° C. for 1.5 hours. The reaction mixture was cooled to ambient temperature, extracted with ethyl acetate, the ethyl acetate extracts dried (MgSO$_4$) and evaporated. The residue was purified by flash column chromatography on silica gel (Merck Art No 9385) using a 40:60:0.2 mixture of ethyl acetate, hexane and triethylamine as eluent to give an oil. The oil was dissolved in ether and excess ethereal hydrogen chloride added until crystallisation began. The solid was collected by filtration and dried to give N,N-dimethyl-3-[4-butoxy-2-(3-hydroxypropyl)phenoxy]propylamine as a white solid (60 mg), m.p. 118° C.; microanalysis, found: C, 62.4; H, 9.6; N, 4.0% $C_{18}H_{32}NO_3Cl$ requires: C, 62.5; H, 9.32; N, 4.05%; NMR ([CD$_3$]$_2$SO+CD$_3$COOD): 0.95(3H,t), 1.45(2H,m), 1.7(4H,m), 2.2(2H,m), 2.58(2H,t), 2.89(6H,s), 3.35(2H,t), 3.55(2H,t), 3.9(2H,t), 4.02(2H,t), 6.72(2H,m) and 6.82(1H,s); m/z 310(M+H).

The N,N-dimethyl-3-(2-allyl-4-butoxyphenoxy) propylamine used as starting material was prepared as described in Example 102:

EXAMPLE 102

Sodium hydride (106 mg) was added to a solution of 2-allyl-4-butoxyphenol (500 mg) in toluene (40 ml). The reaction mixture was heated to reflux. A solution of 3-dimethylaminopropyl chloride (437 mg) in toluene (20 ml) was added to the refluxing reaction mixture and heating continued for a further 8 hours. The reaction mixture was cooled to ambient temperature, evaporated and the residue dissolved in water (10 ml). The resulting solution was extracted with ethyl acetate (4×15 ml). The ethyl acetate extracts were combined, dried (MgSO$_4$) and evaporated to give an oil which was further purified by flash column chromatography on silica gel (Merck Art No 9385) using a 50:50:0.1 mixture of ethyl acetate, hexane and triethylamine as eluent to give N,N-dimethyl-3-(2-allyl-4-butoxyphenoxy) propylamine as yellow oil (556 mg); microanalysis, found: C, 74.5; H, 10.2; N, 4.8% $C_{18}H_{29}NO_2$ requires: C, 74.2; H, 10.0; N, 4.8%; NMR([CD$_3$]$_2$SO): 0.91(3H,t), 1.42(2H,m), 1.65(2H,m), 1.82(2H,m), 2.15(6H,s), 2.38(2H,t), 3.27(2H, d), 3.88(4H,m), 5.2(2H,m), 5.92(1H,m), 6.7(2H,m) and 6.82 (1H,m); m/z 292(M+H).

EXAMPLE 103

A solution of N-isopropyl-3-(2-allyl-4-butoxy-phenoxy) propylamine (404 mg) in ethanol (15 ml) was hydrogenated at ambient temperature and pressure for 8 hours using a catalyst of palladium on carbon (10% w/w, 80 mg). The catalyst was removed by filtration and the filtrate evaporated to give a yellow oil. The oil was purified by flash column chromatography on silica gel (Merck Art No 9385) using a 70:30:1 mixture of ethyl acetate, hexane and triethylamine to give an oil. The oil was dissolved in ether and excess ethereal hydrogen chloride was added until crystallisation began. The solid was collected by filtration and recrystallised from ethyl acetate to give N-isopropyl-3-(4-butoxy-2-propylphenoxy)propylamine (271 mg) as a white solid, m.p. 102 103° C.; microanalysis, found: C, 65.7; H, 10.2; N, 4.0%; $C_{19}H_{34}NO_2Cl$. $0.25H_2O$ requires: C, 65.5; H, 9.98; N, 4.02%; NMR ($[CD_3]_2SO$): 0.90(6H,m), 1.28(6H,d), 1.52 (6H,m), 2.12(2H,m), 2.5(2H,m), 3.04(2H,m), 3.3(1H,m), 3.88(2H,t), 4.0(2H,t), 6.7(2H,t) and 6.85(1H,d); m/z 308 (M+H).

The N-isopropyl-3-(2-allyl-4-butoxyphenoxy) propylamine used as starting material was prepared as described in Example 22.

EXAMPLE 104

A suspension of aluminium chloride (7.95 g) in ether (25 ml) was added to a stirred suspension of lithium aluminium chloride (2.02 g) in ether (45 ml). A solution of 3-(4-chlorophenoxy)propionitrile (10. 4 g) in ether (75 ml) was then added to the stirred suspension in a dropwise fashion over a period of 0.5 hours. The reaction mixture was allowed to reflux during the addition and was stirred for a further 0.75 hours after the addition was complete. Water (20 ml) was slowly added to the cooled reaction mixture, followed by sodium hydroxide solution (0.001M, 10 ml). The resulting precipitate was collected by filtration, washed with ethyl acetate and the filtrate dried using phase separating paper and evaporated to give 3-(4-chlorophenoxy)propylamine as an oil (7.5 g). Treatment of this oil with ethereal hydrogen chloride solution gave a solid which was recrystallised from ethanol to yield the hydrogen chloride salt of 3-(4-chlorophenoxy)propylamine as a solid (1.6 g), m.p. 182° C.; microanalysis, found: C, 48.5; H, 5.9; N, 6.3, Cl 31.6%; $C_9H_{12}ONCl.HCl$ requires: C, 48.6; H, 5.9; N, 6.3; Cl, 32.0%.

The starting material was prepared as follows:

A mixture of p-chlorophenol (25 g), acrylonitrile (30 ml) and a solution of benzyltrimethylammonium hydroxide (8 ml of a 40 wt % solution in methanol) were heated at reflux over the weekend. The reaction mixture was poured into water and extracted with ethyl acetate. The ethyl acetate extract was dried and evaporated to give 3-(4-chlorophenoxy)propionitrile.

EXAMPLE 105

A mixture of N-[3-(4-benzyloxyphenoxy)propyl] phthalimide (3.87 g) and hydrazine hydrate (0.55 g) in ethanol (40 ml) was heated at reflux for 3 hours. The reaction mixture was allowed to cool, filtered and the filtrate evaporated. Sodium hydroxide solution (2M, 20 ml) was added to the residue, the aqueous mixture extracted with ethyl acetate and the ethyl acetate extract dried. The solid collected by filtration of the cooled reaction mixture was suspended in sodium hydroxide solution (2M, 20 ml) and extracted with ethyl acetate. The ethyl acetate extract was dried, combined with the dried ethyl acetate derived from the filtrate and the combined extract evaporated to give 3-(4-benzyloxyphenoxy)propylamine as a solid (1.5 g), m.p. 115° C.

The starting material was prepared as follows.

p-Benzyloxyphenol (10 g) was added to a stirred mixture of sodium hydride (2.64 g of a 50% oil suspension previously washed to remove oil) in dry dimethylformamide (100 ml) under an atmosphere of nitrogen. The reaction mixture was heated at 40° C. for 15 minutes. A solution of N-(3-bromopropyl)phthalimide (14.7 g) in dry dimethylformamide (50 ml) was then added in a dropwise manner to the stirred reaction mixture. The reaction mixture was stirred at ambient temperature overnight. The reaction mixture was then poured into iced water and the resulting aqueous mixture extracted with ethyl acetate. The ethyl extract phase was separated and filtered to give a solid which was recrystalised from ethyl acetate. This solid was combined with the solid obtained after drying and evaporating the filtrate. There was thus obtained N-[3-(4-benzyloxyphenoxy)propyl] phthalimide (12. 6 g), m.p. 144°–145° C.

EXAMPLE 106

A solution of 2-(3-N-isopropylaminopropoxy)-5-butoxy benzaldehyde (150 mg 0.5 mmol) in dry tetrahydrofuran (5 ml) under an atmosphere of argon was added dropwise at a temperature below 10° C. to a stirred solution of phenyl magnesium bromide in diethylether (3M, 10 ml). The reaction mixture was stirred overnight at ambient temperature. The reaction mixture was added to an ice-cold aqueous ammonium chloride solution (20 ml). The solution was extracted with ethyl acetate (2×25 ml), the ethyl acetate extracts combined, dried ($MgSO_4$) and evaporated. The residue was purified by chromatography on silica gel (Merck Art No 7736) using a gradient of 0 to 20% methanol in methylene chloride as eluent to give 2-(α-hydroxybenzyl)-4-butoxy-1-(3-isopropylaminopropoxy)benzene as a solid (20 mg), m.p.t. 117.5° C.

EXAMPLE 107

A solution of 2-(3-[N-isopropylamino]propoxy)-5-butoxybenzaldehyde (150 mg) in dry tetrahydrofuran (5 ml) was added dropwise to a stirred solution of ethyl magnesium bromide in tetrahydrofuran (3H, 10 ml) at a temperature below 10° C. under an atmosphere of argon. The reaction mixture was stirred overnight at ambient temperature. The reaction mixture was poured into ice-cold aqueous ammonium chloride solution (20 ml). The solution was extracted with ethyl acetate (2×25 ml), the ethyl acetate extracts combined, dried ($MgSO_4$) and evaporated. The residue was treated with an excess of anhydrous saturated methanolic hydrogen chloride solution and crystallised from a mixture of toluene/hexane to give N-isopropyl-3-(4-butoxy-2-[1-hydroxypropyl]phenoxy)propylamine hydrochloride as a solid (80 mg), m.p. 104.2° C.

EXAMPLE 108

Sodium borohydride (60 mg) was added portionwise over a period of 15 minutes to a stirred solution of 2-(3-[N-isopropylamino]propxy)-5-butoxybenzaldehyde (100 mg) in methanol (20 ml) and sodium bicarbonate (10 ml). Ethyl acetate (50 ml) was added to the reaction mixture, the organic phase separated, dried ($MgSO_4$) and evaporated to give 2-(3-[N-isopropylamino]propoxy)-5-butoxybenzyl alcohol (70 mg), m.p. 117.8° C.

EXAMPLE 109

A solution of phenyl boronic acid (0.36 g) in ethanol (3.0 ml) was added to a stirred suspension of N-isopropyl-3-(3- bromophenoxy)propylamine (1.0 gm) and tetrakis(triphenylphosphine)-palladium (100 mg) in aqueous 2M sodium carbonate (4.0 ml) and toluene (6.5 ml) under an atmosphere of argon. The mixture was heated at reflux for 18 hours and then cooled to ambient temperature. The reaction mixture was diluted with ethyl acetate, washed with aqueous 2M sodium hydroxide and the organic phase was evaporated to give a solid. The solid was dissolved in hot ethanol, the solution was filtered, and the filtrate evaporated to give a residue which was purified by dry-flash column chromatography on silica gel (Merck 60H, Art No 7736) using ethyl acetate initially followed by ethyl acetate/1% triethylamine as eluent. There was thus obtained an oil which was treated with ethereal hydrogen chloride to give a solid which was recrystallised from isopropyl alcohol to give N-isopropyl-3-(3-phenylphenoxy)propylamine hydrogen chloride (0.26 g) as a solid, m.p. 147°–149° C.; microanalysis, found: C, 70.7; H, 7.9; N, 4.7; Cl, 11.5%; $C_{18}H_{23}NO$. HCl requires: C, 70.7; H, 7.91; N, 4.58; Cl, 11.6%; NMR$(CD_3)_2SO)$: 1.27 (6H,d), 2.16(2H,m), 3.05(2H,br.m), 3.30(1H,m), 4.18(2H,t), 6.96(1H,d of d), 7.24(2H,d of d), 7.31–7.52(4H,m), 7.67 (2H,d of d) and 9.07(1H,br.s); m/z 270(M+H).

The N-isopropyl-3-(3-bromophenoxy)propylamine used as starting material was prepared from 3-bromophenol and 1,3-dibromopropane using the method described in Example 1.

EXAMPLE 110

2-Methylphenyl boronic acid (0.42 g) was added to a solution of N-isopropyl-3-(4-bromophenoxy)propylamine (1.0 g) and tetrakis triphenylphosphine palladium (100 mg) in aqueous 2M sodium carbonate (8.4 ml) and dimethoxyethane (5 ml). The mixture was heated at 80° C. for 18 hours, cooled to ambient temperature and diluted with ethyl acetate. The reaction mixture was washed with dilute sodium hydroxide solution, brine, dried ($MgSO_4$) and evaporated. The residue was purified by dry flash column chromatography on silica gel (Merck 60H, Art No 7736) using a 5:95 v/v mixture of methanol and dichloromethane to give an oil. This oil was treated with ethereal hydrogen chloride to give a solid which was recrystallised from isopropyl alcohol to give N-isopropyl-3-[4-(2-methylphenyl)phenoxy]propylamine hydrogen chloride (0.38 g) as a solid, m.p. 157°–158° C.; microanalysis, found: C, 71.6; Hi 8.2; N, 4.4; Cl, 10.8%; $C_{19}H_{25}NO$. HCl requires: C, 71.3; H, 8.19; N, 4.38; Cl, 11.1%; NMR$([CD_3]_2SO)$: 1.27(6H,d), 2.14(2H,m), 2.22(3H,s), 3.05(2H,t), 3.29(1H, m), 4.13(2H,t), 7.01(2H,d) and 7.12–7.30(6H,m); m/z 284 (M+H).

The 2-methylphenyl boronic acid was prepared as follows:

A solution of 2-bromotoluene (1.0 g) in dry tetrahydrofuran (50 ml) was cooled to −70° C. under an atmosphere of argon. A solution of tert-butyl lithium in pentane (1.7M, 7.6 ml) was added dropwise to the mixture whilst maintaining the temperature below −60° C. The reaction mixture was stirred at −70° C. for 0.5 hours. Trimethyl borate (0.73 ml) was added and the mixture allowed to warm to ambient temperature. The mixture was poured onto a mixture of aqueous 2M hydrochloric acid and ice, and the mixture extracted with ethyl acetate. The ethyl acetate extract was washed with brine, dried ($MgSO_4$) and evaporated to give 2-methylphenylboronic acid as a white solid (0.48 g) which was used without further purification.

EXAMPLE 111

A mixture of benzyl-4-[3-(N-methyl-N-isopropylamino)-propoxy]benzoate hydrogen chloride (300 mg), isopropyl alcohol (20 ml) and a catalyst of palladium on carbon (10% w/w, 30 mg) was hydrogenated at ambient temperature and pressure for 16 hours. Ethanol was then added to dissolve precipitated product and the mixture was then filtered to remove inorganic material. The filtrate was evaporated to give 4-[3-(N-methyl-N-isopropylamino)propoxy]benzoic acid hydrogen chloride as a solid (172 mg), m.p. 167.8° C.; microanalysis, found: C, 56.2; H, 7.40; H, 4.70; N, 4.70%, $C_{14}H_{21}NO_3$. HCl $0.6H_2O$ requires C, 56.3; H, 7.87; N, 4.63%; NMR$([CD_3]_2SO)$: 1.2–1.35(6H,q), 2.1–2.4(2H,m), 2.6–2.7(3H,d), 3.0–3.65(3H,m), 4.1–4.2(2H,t). 7.0–7.1(2H, d), 7.85–7.95(2H,d) and 10.5–10.8(1H, br s); m/z 252 (M+H).

The benzyl-4-[3-(N-methyl-N-isopropylamino)propoxy] benzoate used as starting material was prepared as described in Example 50.

EXAMPLE 112

A solution of N-isopropyl-3-(2-allylphenoxy) propylamine hydrobromide (313 mg) in ethanol was hydrogenated at ambient temperature and pressure for 3 hours using a catalyst of palladium on carbon (10% w/w, 30 mg). The catalyst was removed by filtration and the filtrate evaporated to give a solid which was crystallised from a mixture of propan-2-ol and diethyl ether to give N-isopropyl-3-(2-propylphenoxy)propylamine hydrogen bromide as a colourless solid (204 mg), m.p. 89°–90°; microanalysis, found: C, 56.6; H, 8.2; N, 4.43%; $C_{15}H_{25}NO$.HBr requires: C,57.0; H, 8.3; N, 4.70%; NMR($[CD_3]_2SO$): 0.92(3H,t), 1.25(6H,d), 1.55(2H,m), 2.10(2H, m), 2.51(2H,m), 3.10(2H,t), 3.31(1H,m), 4.05(2H,t), 6.90 (2H,m), 7.13(1H,m) and 8.46(2H,m); m/z 236(M+H).

The N-isopropyl-3-(2-allylphenoxy)propylamine used as starting material was prepared as described in Example 4.

EXAMPLES 113–114

The method described in Example 1 was repeated using allylamine in place of isopropylamine to give the following products of formula 3 in which $R^1$=H, $R^2$=allyl, $Y^3$=$Y^5$=$Y^6$=H:

| Ex | $Y^2$ | $Y^4$ | SALT | M.PT. (°C.) |
|---|---|---|---|---|
| 113 | allyl | MeCONH | HBr | 107.7 |
| 114 | allyl | MeCO | oxalate | 208–209 |

EXAMPLE 115

The method described in Example 1 was repeated using 1-bromo-3-chloro-2-methylpropane in place of 1,3-dibromopropane, except the reaction of the corresponding phenoxypropylchloride intermediate was treated with isopropylamine for a period of five days in the presence of potassium iodide. There was thus obtained 3-allyl-4-[3-(N-isopropylamino)-2-methylpropoxy]acetanilide microanalysis, found: C, 69.4; H, 9.32; N, 8.94%; $C_{18}H_{28}N_2O_2$. $0.4H_2O$ requires: C, 69.4; H, 9.4; N, 8.7%; NMR$([CD_3]_2SO)$: 0.98(6H,d of d), 1.97(3H,s), 2.55–2.76 (3H,m), 3.28(2H,d), 3.84(2H,m), 4.96–5.10(2H,m), 5.91 (1H,m), 6.85(1H,d), 7.26(1H,d), 7.39(1H,d of d) and 9.67 (1H,s); m/z 305(M+H).

EXAMPLE 116

The method described in Example 1 was repeated using 1,3-dibromobutane in place of 1,3-dibromopropane. There was thus obtained a mixture of 3-allyl-4-[3-(N-isopropylamino)-3-methylpropoxy]acetanilide and 3-allyl-4-[3-(N-isopropylamino)-1-methylpropoxy]acetanilide. These isomers were separated by flash column chromatography on silica gel (Merck Art. No 9385) using a 5:95:1 mixture of methanol/dichloromethane/triethylamine as eluent to give 3-allyl-4-[3-(N-isoproylamino)-3-methylpropoxy]acetanilide as a solid, m.p. 74°–75.5° C.; NMR[(CD$_3$)2SO]: 0.98(9H,m), 1.72(2H,m), 1.97(3H,s), 2.88(2H,m), 3.29(2H,d), 3.99(2H,m), 4.97–5.10(2H,m), 5.90(1H,m), 6.85(1H,d), 7.27(1H,d), 7.38(1H,d of d), 9.67 (1H,s); $C_{18}H_{28}N_2O_2 \cdot 0.3H_2O$ requires: C, 69.8; H, 9.3; N, 9.04; found: C,69.6; H, 9.3; N, 9.1; m/z 305(H+H); and 3-allyl-4-[3-(N-isoproylamino)-1-methylpropoxy] acetanilide as an oil; NMR[(CD$_3$)$_2$SO]: 0.95(6H,d of d), 1.20(3H,d), 1.73(2H,m), 1.97(3H,s), 2.55–2.75(3H,m), 3.28 (2H,d), 4.48(1H,m), 4.97–5.11(2H,m), 5.91(1H,m), 6.90 (1H,d), 7.27(1H,d), 7.38(1H,d of d), 9.67(1H,s). $C_{18}H_{28}N_2O_2$ 0.25H$_2$O requires: C, 70.0; H, 9.30; N, 9.07%; found: C, 70.1; H, 9.5; N, 9.1%; m/z 305(H+H).

EXAMPLE 117

The procedure described in Example 102 was repeated using 2-phenylphenol in place of 2-allyl-4-butoxyphenol to give N,N-dimethyl-3-(2-phenylphenoxy)propylamine, which on conversion to the hydrogen chloride salt, gave a solid, m.p. 53°–54° C.

EXAMPLES 118–119

The procedure described in Example 1 was repeated using the appropriate amine to give the following compounds of formula 3 in which $Y^3=Y^5=Y^6=H$:

| Ex  | –NR$^1$R$^2$ | Y$^2$ | Y$^4$   | SALT      | M.PT(°C.) |
|-----|--------------|-------|---------|-----------|-----------|
| 118 | Pyrrolidino  | allyl | MeCONH  | free base | 93–94     |
| 119 | morpholino   | allyl | MeCONH  | free base | 90–91     |

EXAMPLE 121

A solution of N,N-diethyl-3-(3-benzyloxyphenoxy) propylamine (0.7 g) in ethanol was treated with ethereal hydrogen chloride solution and the mixture hydrogenated in the presence of Pd/C (0.25 g, 5% w/w) for 2 hours. The catalyst was removed by filtration and the filtrate evaporated. The residue was crystallised from a mixture of ethanol and ether to give N,N-diethyl-3-(3-hydroxyphenoxy) propylamine (0.4 g), m/z 223.

The N,N-diethyl-3-(3-benzyloxyphenoxy)propylamine used as starting material was prepared using the method described in Example 102 but using 3-benzyloxyphenol in place of 2-allyl-4-butoxyphenol.

EXAMPLES 122–123

The procedure described in Example 1 was repeated using the appropriate phenol of formula 1 and ammonia in place of isopropylamine to give the following compounds of formula 3 in which $R^1=R^2=H$, $Y^3=Y^5=Y^6=H$:

| Example | Y$^2$ | Y$^4$ | SALT | M.PT (°C.) |
|---------|-------|-------|------|------------|
| 122     | H     | BuO   | HCl  | 197–198    |
| 123     | allyl | H     | HCl  | 106–107    |

EXAMPLE 124

Illustrative pharmaceutical dosage forms suitable for presenting the compounds of the invention for therapeutic or prophylactic use include the following tablet and capsule formulations, which may be obtained by conventional procedures well known in the art of pharmacy and are suitable for therapeutic or prophylactic use in humans:

|                                                  | mg/tablet |
|--------------------------------------------------|-----------|
| (a) Tablet I                                     |           |
| Compound Z*                                      | 1.0       |
| Lactose Ph. Eur.                                 | 93.25     |
| Croscarmellose sodium                            | 4.0       |
| Maize starch paste (5% w/v aqueous paste)        | 0.75      |
| Magnesium stearate                               | 1.0       |
| (b) Tablet II                                    |           |
| Compound Z*                                      | 50        |
| Lactose Ph. Eur                                  | 223.75    |
| Croscarmellose sodium                            | 6.0       |
| Maize starch                                     | 15.0      |
| Polyvinylpyrrolidone (5% w/v aqueous paste)      | 2.25      |
| Magnesium stearate                               | 3.0       |
| (c) Tablet III                                   |           |
| Compound Z*                                      | 100       |
| Lactose Ph. Eur.                                 | 182.75    |
| Croscarmellose sodium                            | 12.0      |
| Maize starch paste (5% w/v aqueous paste)        | 2.25      |
| Magnesium stearate                               | 3.0       |
| (d) Capsule                                      |           |
| Compound Z*                                      | 10        |
| Lactose Ph.Eur.                                  | 488.5     |
| Magnesium stearate                               | 1.5       |

Note
*The active ingredient Compound Z is a compound of formula I, or a salt thereof, for example a compound of formula I described in any of the preceding Examples.

The tablet compositions (a)–(c) may be enteric coated by conventional means, for example, with cellulose acetate phthalate.

CHEMICAL FORMULAE

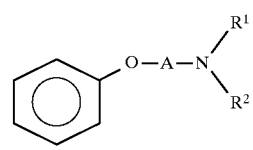

I

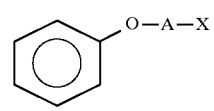

II

IIa

III

-continued
CHEMICAL FORMULAE

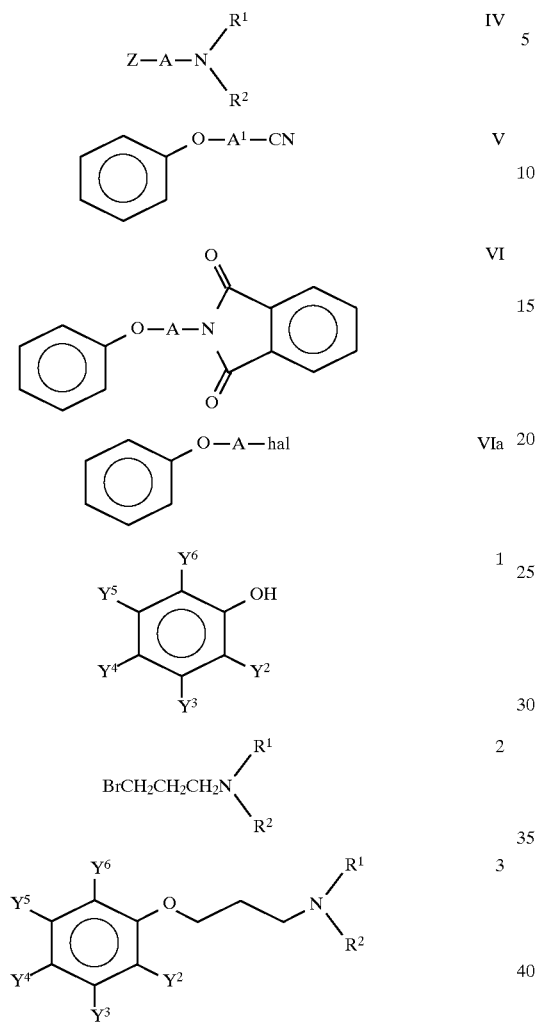

We claim:

1. A method for inhibiting cholesterol biosynthesis in a warm blooded animal in need thereof, said method comprising administering to said animal a cholesterol biosynthesis inhibiting effective amount of a compound of formula I

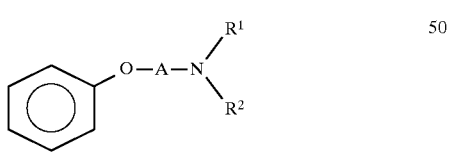

or a pharmaceutically acceptable salt thereof, wherein:
$R^1$ and $R^2$ are independently selected from hydrogen, (1–10C)alkyl) and (2–10C)alkenyl;
A is trimethylene which is optionally substituted by one or more (14C)alkyl groups; and
the phenyl ring bears a substituent selected from (1–6C)alkanoylamino and N-[(1–6C)alkyl](1–6C)alkanoylamino, and is optionally further substituted by one or more substituents independently selected from halogeno, hydroxy, hydroxy(1–6C)alkyl, amino, (1–6C)alkylamino, di-[(1–6C)alkyl]amino, nitro, cyano, carboxy, carbamoyl, N-(1–6C)alkylcarbamoyl, di-N,N-[(1–6C)alkyl]carbamoyl, carbamoyl(1–4C)alkyl, N-(1–6C)alkylcarbamoyl(1–4C)alkyl, di-N,N-[(1–6C)alkyl]carbamoyl(1–4C)alkyl, sulphamoyl, N-(1–6C)alkylsulphamoyl, di-N,N-[(1–6C)alkyl] sulphamoyl, sulphamoyl(1–4C)alkyl, N-(1–6C)alkylsulphamoyl(1–4C)alkyl, di-N,N-[(1–6C)alkyl]sulphamoyl(1–4C)alkyl, ureido, N'-(1–6C)alkylureido, (1–10C)alkyl optionally containing one or more double bonds, (2–6C)alkynyl, (1–6C)alkoxycarbonyl, (1–6C)alkanoyl and oxime derivatives thereof and O-(1–6C)alkyl ethers of said oxime derivatives, (1–6C)alkanoylamino, N-[(1–6C)alkyl](1–6C)alkanoylamino, (1–6C)alkoxy, (1–6C)alkoxy(1–4C)alkyl, (1–6C)alkylthio, (1–6C)alkylsulphinyl, (1–6C)alkylsulphonyl and halogeno(1–6C)alkyl.

2. The method as claimed in claim 1 wherein $R^1$ and $R^2$ are independently selected from hydrogen, methyl, ethyl, propyl, isopropyl, butyl, isobutyl, sec-butyl, t-butyl, allyl, prop-2-enyl, but-2-enyl and 2-methyl-2-propenyl;
A is trimethylene optionally bearing one or two groups selected from methyl and ethyl; and
the phenyl ring bears a substituent selected from formamido, acetamido, propionamido, iso-propionamido, butyramido, iso-butyramido, N-methylacetamido, N-ethylacetamido, N-methylpropionamido, N-ethylpropionamido, N-methylbutyramido, and is optionally further substituted by one or more substituents independently selected from hydroxy, amino, nitro, cyano, carboxy, carbamoyl, sulphamoyl, fluoro, chloro, bromo, iodo, hydroxymethyl, 2-hydroxyethyl, 3-hydroxypropyl, 1-hydroxypropyl, 1-hydroxyethyl, methylamino, ethylamino, propylamino, butylamino, dimethylamino, diethylamino, methylpropylamino, methylethylpropylamino, N-methylcarbamoyl, N-ethylcabamoyl, N-propylcarbamoyl, N,N-dimethylcarbamoyl, N,N-diethylcarbamoyl, carbamoylmethyl, carbamoylethyl, N-methylcarbamoylmethyl, N-ethylcarbamoylmethyl, N-methylcarbamoylethyl, N,N-dimethylcarbamoylmethyl, N,N-diethylcarbamoylmethyl, N-methylsulphamoyl, N-ethylsulphamoyl, N-propylsulphamoyl, N,N-dimethylsulphamoyl, N,N-diethylsulphamoyl, sulphamoylmethyl, sulphamoylethyl, N-methylsulphamoylmethyl, N-ethylsulphamoylmethyl, N-methylsulphamoylethyl, N,N-dimethylsulphamoylmethyl, N,N-diethylsulphamoylmethyl, N'-methylureido, N'-ethylureido, N'-propylureido, N'-isoproplyureido, N'-butylureido, allyl, prop-2-enyl, but-2-enyl, 2-methyl-2-propenyl, 2,6-hexadienyl, geranyl, methyl, ethyl, propyl, isopropyl, butyl, isobutyl, sec-butyl, prop-2-ynyl, but-2-ynyl, methoxycarbonyl, ethoxycarbonyl, propoxycarbonyl, formyl, acetyl, propionyl, butyryl, formamido, acetamido, propionamido, iso-propionamido, butyramido, iso-butyramido, N-methylacetamido, N-ethylacetamido, N-methylpropionamido, N-ethylpropionamido, N-methylbutyramido, methoxy, ethoxy, propoxy, isopropoxy, butoxy, methylpropoxy, ethylethoxy, methymethoxy, ethylethoxy, ethylpropoxy, methylthio, ethylthio, propylthio, isopropylthio, butylthio, methylsulphinyl, ethylsulphinyl, propylsulphinyl, isopropylsulphinyl, butylsulphinyl, methylsulphonyl, ethylsulphonyl, isopropylsulphonyl, butylsulphonyl and α-hydroxybenzyl.

3. A method for inhibiting cholesterol biosynthesis in a warm blooded animal in need thereof, said method comprising administering to said animal a cholesterol biosynthesis inhibiting effective amount of a compound of formula I

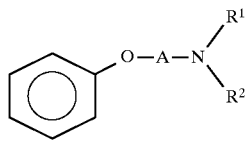

or a pharmaceutically acceptable salt thereof, wherein:
$R^1$ and $R^2$ are independently selected from hydrogen and (1–6C) alkyl;
A is trimethylene; and
the phenyl ring bears a substituent selected from (1–6C) alkanoylamino and N-[(1–6C)alkyl](1–6C)alkanoylamino, and is optionally further substituted by one or more substituents selected from halogeno, (1–6C)alkyl optionally containing one or more double bonds, (2–6C)alkynyl, (1–6C)alkoxycarbonyl, (1–6C)alkanoylamino, N-[(1–6C)alkyl](1–6C)alkanoylamino, (1–6C)alkoxy, (1–6C)alkylthio, (1–6C)alkylsulphinyl and (1–6C)alkylsulphonyl.

4. The method as claimed in claim 1 wherein $R^1$ is hydrogen.

5. The method as claimed in claim 1 wherein $R^1$ is hydrogen and $R^2$ is isopropyl.

6. The method as claimed in claim 1 wherein the phenyl ring bears a substituent selected from (1–6C)alkanoylamino and N-[(1–6C)alkyl]alkanoylamino and is optionally further substituted by two or three substituents independently selected from (2–6C)alkenyl, halogeno, amino, cyano, ureido, (1–6C)alkyl carbamoyl(1–4C)alkyl, (1–6C)alkanoylamino, (1–6C)alkoxycarbonyl, N-[(1–6C)alkyl](1–6C)alkanoylamino, (1–6C)alkanoyl and oxime derivatives thereof and O-(1–6C)alkyl ethers of said oxime derivatives.

7. The method as claimed in claim 1 wherein $R^1$ is hydrogen, $R^2$ is isopropyl, A is trimethylene, and the phenyl ring bears a (1–6C)alkanoyl substituent and is optionally further substituted by one or more substituents selected from (2–6C)alkenyl, (1–6C)alkanoylamino, halogeno, carbamoyl (1–4C)alkyl, (1–6C)alkyl, and a group of formula —C(Ra)=NORb wherein Ra and Rb are (1–6C)alkyl.

8. The method of claim 1 wherein the compound is selected from:
N-isopropyl-3-(4-acetamido-2-allylphenoxy) propylamine;
N-methyl-N-isopropyl-3-(4-acetamido-2-allylphenoxy)-propylamine;
N-cyclopentyl-3-(4-acetamido-2-allylphenoxy) propylamine;
N-cyclobutyl-3-(4-acetamido-2-allylphenoxy) propylamine;
N-isopropyl-3-(2-allyl-4-butyramidophenoxy) propylamine;
N-isopropyl-3-(4-acetamido-2-chlorophenoxy) propylamine;
N-isopropyl-3-(4-acetamido-2-propylphenoxy) propylamine; and
N-isopropyl-3-(4-acetamido-2-allylphenoxy)-1-methylpropylamine;
or a pharmaceutically acceptable salt thereof.

9. The method of claim 1 or 2 wherein said compound or pharmaceutically acceptable salt thereof is administered to said animal in the form of a tablet or capsule.

10. The method as claimed in claim 1 or 2 wherein the phenyl ring bears one or two further substituents independently selected from (2–6C)alkenyl, halogeno, amino, cyano, ureido, (1–6C)alkyl carbamoyl(1–4C)alkyl, (1–6C)alkanoylamino, (1–6C)alkoxycarbonyl; N-[(1–6C)alkyl](1–6C)alkanoylamino, (1–6C)alkanoyl and oxime derivatives thereof and O-(1–6C)alkyl ethers of said oxime derivatives.

11. The method as claimed in claim 1 wherein $R^1$ is hydrogen or (1–4C)alkyl; $R^2$ is isopropyl; A is trimethylene optionally bearing one or two methyl groups; and the phenyl ring bears one or two further substituents independently selected from (2–6C)alkenyl, halogeno, amino, cyano, ureido, (1–6C)alkyl, carbamoyl(1–4C)alkyl, (1–6C)alkanoylamino, (16C)alkoxycarbonyl, N-[(1–6C)alkyl](1–6C)alkanoylamino, (1–6C)alkanoyl and oxime derivatives thereof and O-(1–6C)alkyl ethers of said oxime derivatives.

12. The method as claimed in claim 11 where in $R^1$ is hydrogen or (1–4C)alkyl, $R^2$ is isopropyl; A is trimethylene; and the phenyl ring is selected from the following phenyl moieties:
2-allyl-4-acetamidophenyl;
2-allyl-4-butryamidophenyl; and
2-propyl-4-acetamidophenyl.

13. The method of claim 1 wherein said method for inhibiting cholesterol biosynthesis is used in the treatment of hypercholesterolemia or atherosclerosis.

* * * * *